US010849607B2

(12) United States Patent
Stanley et al.

(10) Patent No.: US 10,849,607 B2
(45) Date of Patent: Dec. 1, 2020

(54) VASCULAR CLOSURE DEVICE SUTURE TENSION MECHANISM

(71) Applicant: Cook Medical Technologies LLC, Bloomington, IN (US)

(72) Inventors: Cleon Stanley, Bloomington, IN (US); Ram H. Paul, Jr., Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 387 days.

(21) Appl. No.: 15/491,205

(22) Filed: Apr. 19, 2017

(65) Prior Publication Data
US 2017/0215853 A1 Aug. 3, 2017

Related U.S. Application Data

(63) Continuation of application No. 14/039,237, filed on Sep. 27, 2013, now abandoned.
(Continued)

(51) Int. Cl.
*A61B 17/00* (2006.01)
*A61B 17/04* (2006.01)
*A61B 17/06* (2006.01)

(52) U.S. Cl.
CPC ...... *A61B 17/0057* (2013.01); *A61B 2017/00623* (2013.01); *A61B 2017/00628* (2013.01);
(Continued)

(58) Field of Classification Search
CPC ...... A61B 17/0057; A61B 2017/00623; A61B 2017/0496; A61B 2017/06176; A61B 2017/00628; A61B 2017/00663
See application file for complete search history.

(56) References Cited

U.S. PATENT DOCUMENTS

| 4,744,364 A | 5/1988 | Kensey |
| 5,021,059 A | 6/1991 | Kensey et al. |

(Continued)

FOREIGN PATENT DOCUMENTS

| EP | 0464480 A1 | 1/1992 |
| EP | 0 534 696 A1 | 3/1993 |

(Continued)

OTHER PUBLICATIONS

International Search Report and Written Opinion issued in PCT/US2012/066173, dated Mar. 8, 2013.
(Continued)

*Primary Examiner* — Elizabeth Houston
*Assistant Examiner* — Michael G Mendoza
(74) *Attorney, Agent, or Firm* — Woodard, Emhardt, Henry, Reeves & Wagner, LLP

(57) ABSTRACT

Systems and methods for sealing an opening in a wall within the body of a patient are disclosed. In one embodiment, the system has an elongated body coupled to a vascular closure device and a resisting member, the elongated body having a high resistance portion and a low resistance portion and being constructed and arranged to interface with a resisting member to apply a conforming force to a vascular closure device. In some exemplary embodiments, the elongated body comprises a large diameter portion positioned in a proximal end region of the elongated body. Methods and other embodiments are disclosed.

21 Claims, 20 Drawing Sheets

Related U.S. Application Data

(60) Provisional application No. 61/736,812, filed on Dec. 13, 2012.

(52) U.S. Cl.
CPC .............. *A61B 2017/00663* (2013.01); *A61B 2017/0496* (2013.01); *A61B 2017/06176* (2013.01)

(56) References Cited

U.S. PATENT DOCUMENTS

| | | | |
|---|---|---|---|
| 5,312,435 | A | 5/1994 | Nash et al. |
| 5,342,393 | A | 8/1994 | Stack |
| 5,343,393 | A | 8/1994 | Stack |
| 5,350,399 | A | 9/1994 | Erlebacher et al. |
| 5,411,520 | A | 5/1995 | Nash et al. |
| 5,531,759 | A | 7/1996 | Kensey et al. |
| 5,545,178 | A | 8/1996 | Kensey et al. |
| 5,620,461 | A | 4/1997 | Muijs Van De Moer |
| 5,662,681 | A | 9/1997 | Nash et al. |
| 5,700,277 | A | 12/1997 | Nash et al. |
| 5,800,436 | A | 9/1998 | Lerch |
| 5,916,236 | A | 6/1999 | Muijs Van de Moer et al. |
| 6,059,800 | A | 5/2000 | Hart et al. |
| 6,071,301 | A | 6/2000 | Cragg et al. |
| 6,190,400 | B1 | 2/2001 | Van De Moer et al. |
| 6,425,911 | B1 | 7/2002 | Akerfeldt |
| 6,508,828 | B1 | 1/2003 | Akerfeldt et al. |
| 6,764,500 | B1 | 7/2004 | Muijs Van De Moer et al. |
| 6,860,895 | B1 | 3/2005 | Akerfeldt et al. |
| 6,939,363 | B2 | 9/2005 | Akerfeldt |
| 7,048,710 | B1 | 5/2006 | Cragg et al. |
| 7,169,168 | B2 | 1/2007 | Muijs Van De Moer et al. |
| 7,338,514 | B2 | 3/2008 | Wahr et al. |
| 7,597,705 | B2 | 10/2009 | Forsberg et al. |
| 7,618,436 | B2 | 11/2009 | Forsberg |
| 7,621,937 | B2 | 11/2009 | Pipenhagen et al. |
| 7,658,748 | B2 | 2/2010 | Marino et al. |
| 7,717,929 | B2 | 5/2010 | Fallman |
| 7,875,052 | B2 | 1/2011 | Kawaura et al. |
| 7,931,671 | B2 | 4/2011 | Paul et al. |
| 2003/0144695 | A1 | 7/2003 | McGuckin, Jr. et al. |
| 2005/0085855 | A1 | 4/2005 | Forsberg |
| 2005/0169974 | A1 | 8/2005 | Tenerz |
| 2005/0251209 | A1* | 11/2005 | Saadat .............. A61B 17/0401 606/232 |
| 2005/0283187 | A1 | 12/2005 | Longson |
| 2006/0142797 | A1 | 6/2006 | Egnelov |
| 2007/0123936 | A1 | 5/2007 | Goldin et al. |
| 2007/0276437 | A1 | 11/2007 | Call et al. |
| 2008/0071310 | A1 | 3/2008 | Hoffman et al. |
| 2008/0097521 | A1 | 4/2008 | Khosravi et al. |
| 2008/0114395 | A1 | 5/2008 | Mathisen et al. |
| 2008/0287986 | A1 | 11/2008 | Thor et al. |
| 2008/0312684 | A1 | 12/2008 | Drasler et al. |
| 2009/0018574 | A1 | 1/2009 | Martin |
| 2009/0054926 | A1 | 2/2009 | Pipenhagen et al. |
| 2009/0088793 | A1 | 4/2009 | Bagaoisan et al. |
| 2009/0112257 | A1 | 4/2009 | Prelnitz |
| 2009/0216267 | A1 | 8/2009 | Willard et al. |
| 2009/0234377 | A1 | 9/2009 | Mahlin |
| 2010/0042144 | A1 | 2/2010 | Bennett |
| 2010/0057110 | A1 | 3/2010 | Lampropoulos et al. |
| 2010/0087854 | A1 | 4/2010 | Stopek et al. |
| 2010/0145365 | A1 | 6/2010 | McLawhorn |
| 2010/0217308 | A1 | 8/2010 | Hansen et al. |
| 2010/0217309 | A1 | 8/2010 | Hansen et al. |
| 2010/0286727 | A1 | 11/2010 | Terwey |
| 2011/0066181 | A1 | 3/2011 | Jenson et al. |
| 2011/0288581 | A1 | 11/2011 | Paul et al. |
| 2012/0116447 | A1 | 5/2012 | Stanley et al. |

FOREIGN PATENT DOCUMENTS

| | | |
|---|---|---|
| EP | 1 169 968 A1 | 1/2002 |
| EP | 1 266 626 A1 | 12/2002 |
| EP | 1 413 255 A1 | 4/2004 |
| EP | 1 440 661 | 7/2004 |
| EP | 2064999 A2 | 6/2009 |
| WO | WO 1999/33402 | 7/1999 |
| WO | WO 2000/078226 | 12/2000 |
| WO | WO 2005/063133 A1 | 7/2005 |
| WO | WO 2006/075228 | 7/2006 |
| WO | WO 2007/059243 A1 | 5/2007 |
| WO | WO 2011/146729 A2 | 11/2011 |

OTHER PUBLICATIONS

International Search Report and Written Opinoin issued in PCT/US2011/037173 dated Nov. 17, 2011.

* cited by examiner

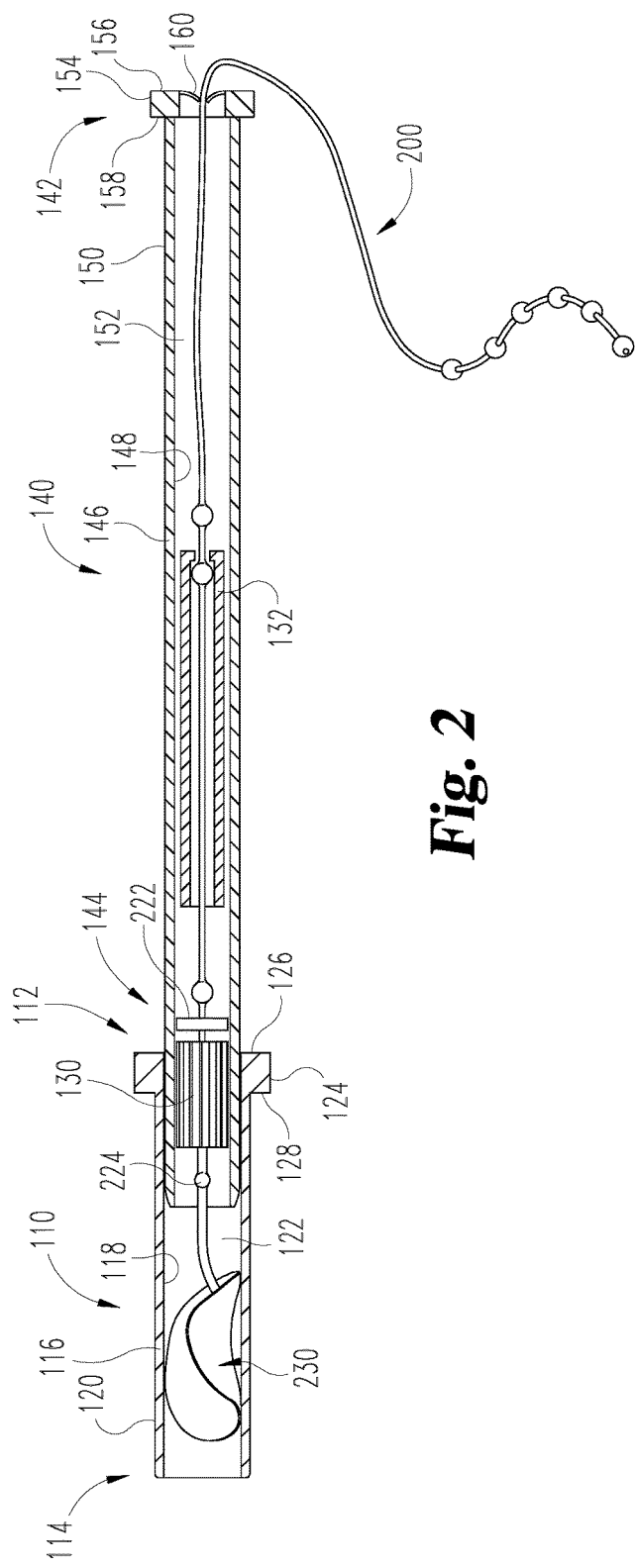
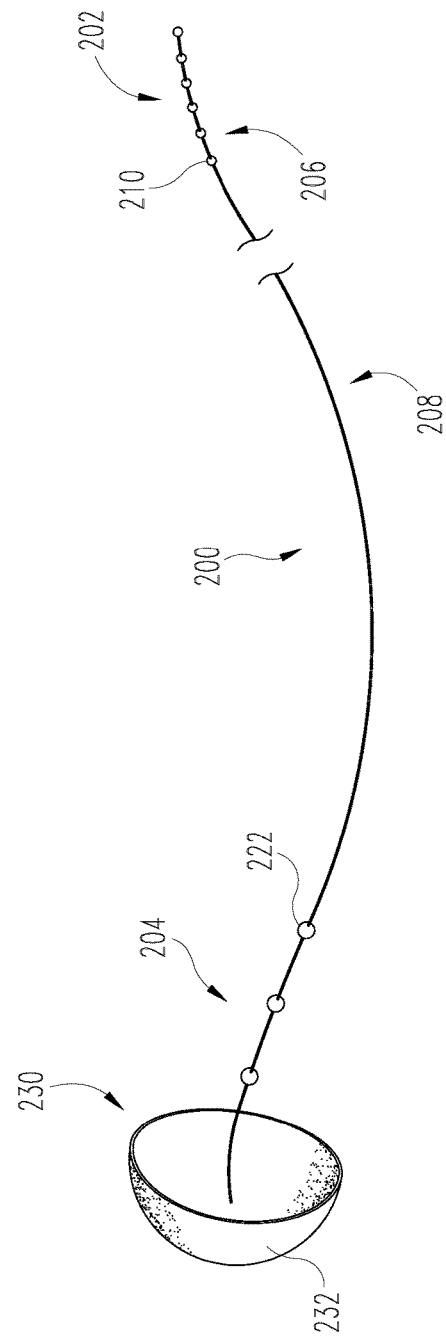

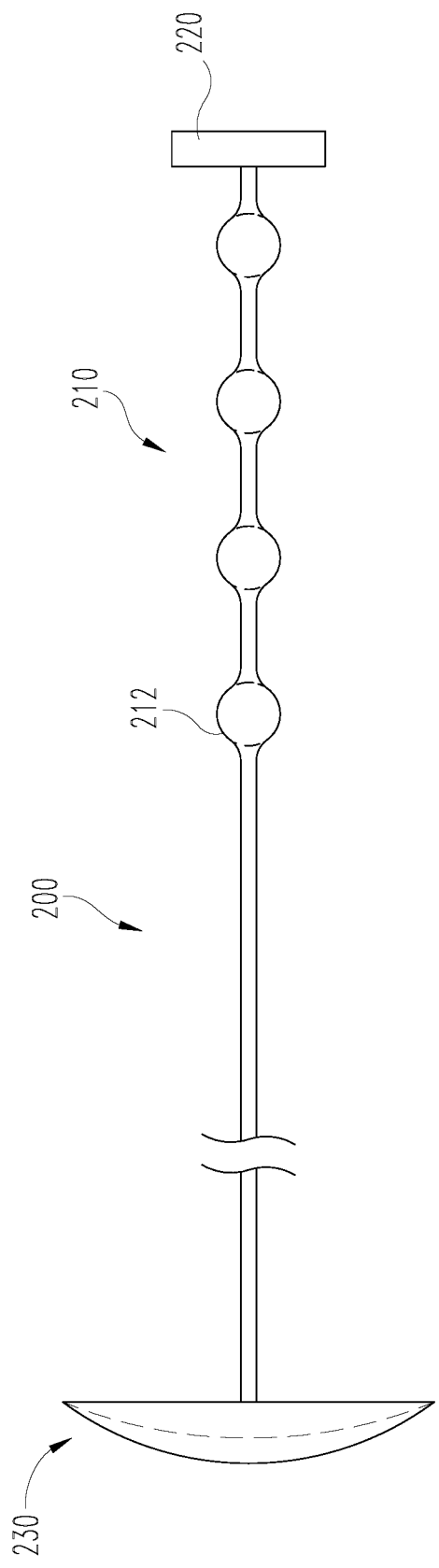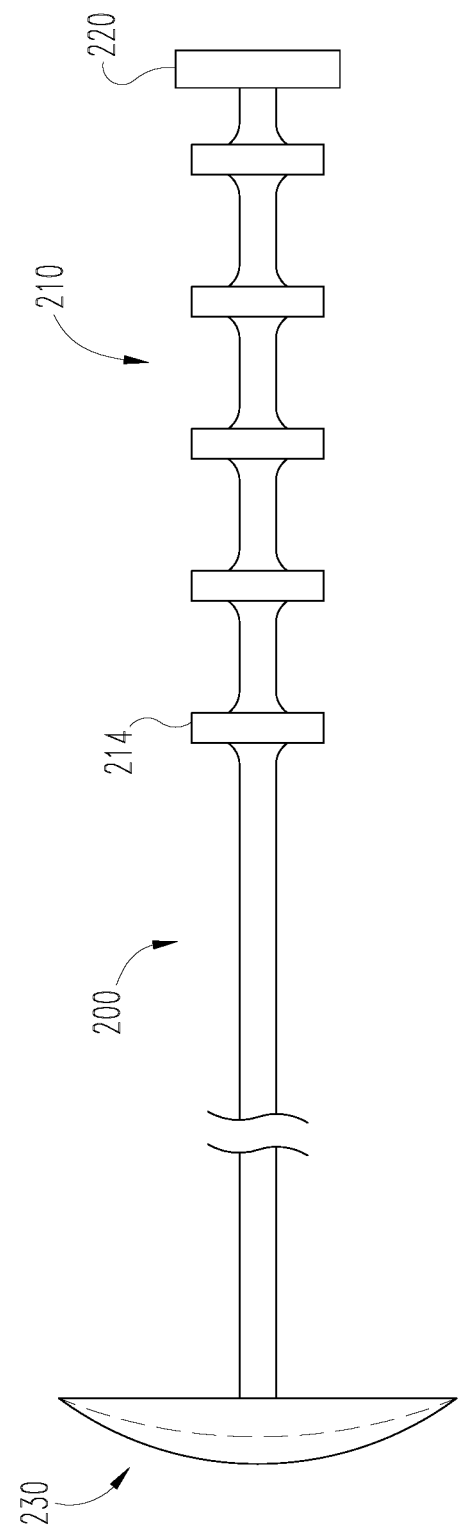

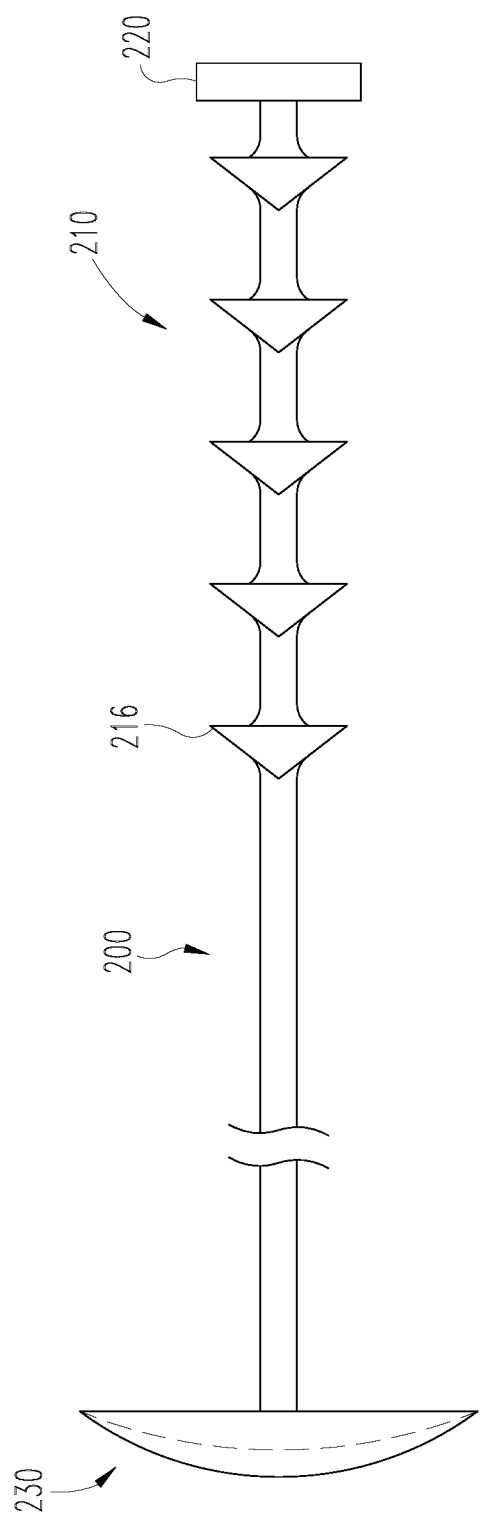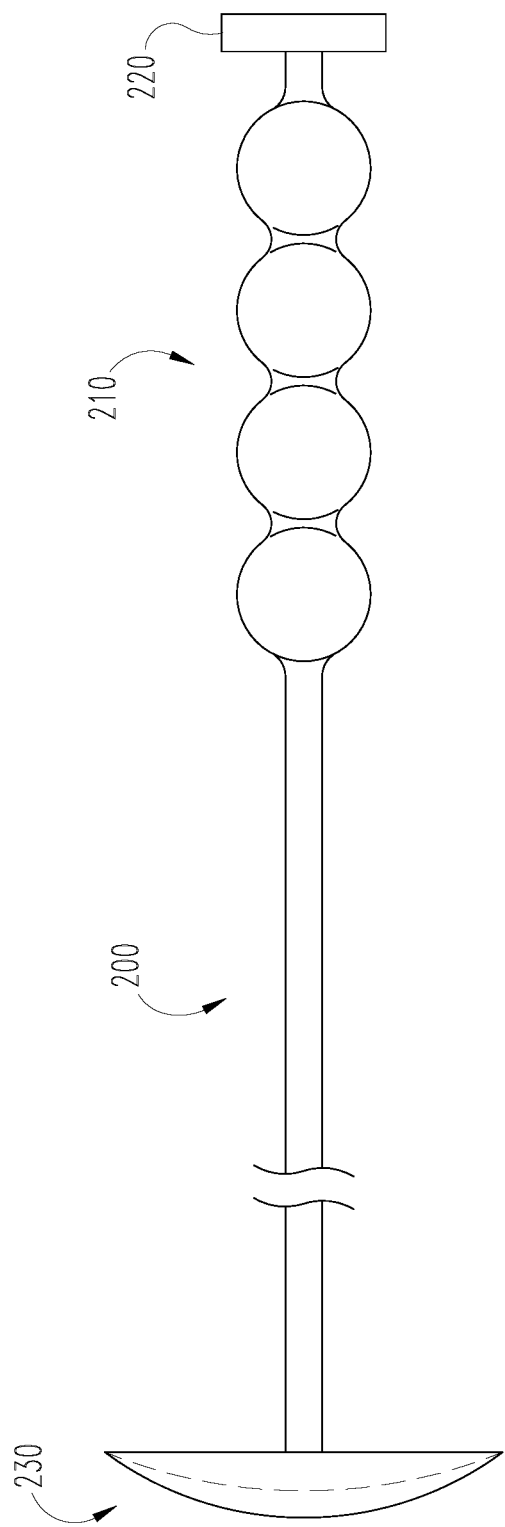

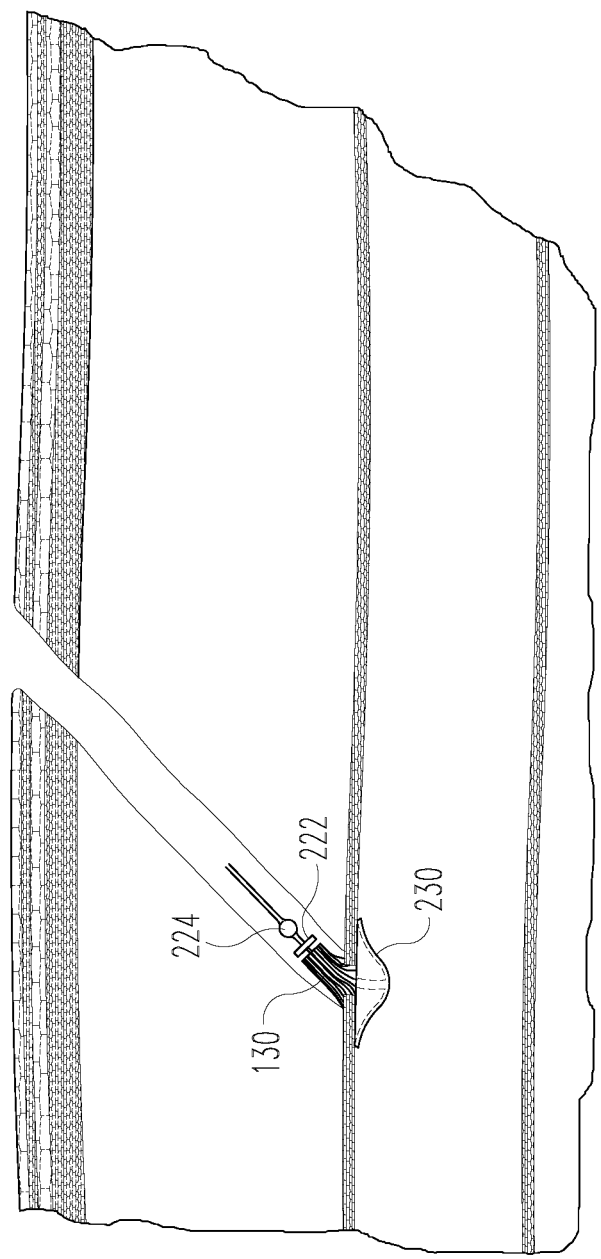

VASCULAR CLOSURE DEVICE SUTURE TENSION MECHANISM

CROSS REFERENCE TO RELATED APPLICATIONS

This application is a continuation application of U.S. patent application Ser. No. 14/039,237 filed Sep. 27, 2013 which claims the benefit of U.S. Provisional Application No. 61/736,812 filed Dec. 13, 2012, which are both hereby incorporated by reference.

FIELD

The present disclosure relates generally to systems and methods for sealing an opening in the body of a patient.

BACKGROUND

This disclosure concerns apparatuses and methods useful for sealing an opening in a bodily wall, such as an access opening in the wall of a blood vessel or a fistula. In particular, apparatus and methods are disclosed for closing and allowing healing of an opening in a tissue wall, whether made during a medical procedure (e.g. those in which apparatus or medicaments are introduced into tissue) or naturally occurring (e.g. as a result of malformation or disease)

It has long been known to insert devices into bodily vessels or conduits to provide therapy or for diagnostic purposes. For example, in cardiovascular medicine, it is known to insert catheters, stents and other devices into a patient's vascular system in order to evaluate or treat the patient. In the case of percutaneous transluminal angioplasty (PTA), an opening is made through the patient's skin and into a large or relatively large blood vessel, such as the femoral artery, and a balloon is inserted into the vessel and advanced to the location where vessel narrowing has occurred, such as by atherosclerosis. Similar procedures are used to implant stents to maintain flow through blood or other bodily vessels or ducts. In accessing the interior of a blood vessel, the interventionalist or medical professional must breach the integrity of the vessel. A variety of devices (e.g. needles, guide wires, cannulae) are known to open a path into a vessel via a percutaneous opening or other approach. Additional devices or implants can be moved through such devices, or through sleeves or cannulae placed in the opening to keep it open, and into the vessel.

When the procedure is concluded, a cannula or other access device is removed from the vessel, leaving an opening in the vessel. If the arteriotomy is not adequately closed, a subcutaneous hematoma will form. The medical professional must therefore take steps to close the opening in the vessel. In some cases, the opening may be sutured closed, but such action can be very difficult in close quarters, and many vessel-accessing procedures are intended to be minimally-invasive to reduce tissue damage. It is also known to apply constant, firm external pressure to the opening in the vessel, particularly if it is a blood vessel, to allow the body's natural coagulation and healing processes to work. In cases in which angioplasty or similar treatment has taken place, however, commonly an anticoagulant has been administered to the patient, making natural closing of the opening in the vessel wall a longer or more difficult process. Maintaining physical pressure on a relatively large blood vessel for a time period sufficient for natural closure also presents at least inconvenience and discomfort to the patient in having to remain still and submit to that pressure, and there is the risk that too much pressure can damage the vessel or tissues that rely on continued flow through it.

Therapies for closing naturally-occurring fistulae or other undesirable bodily openings are also known. Treatments have included closure by suturing or by covering the opening, and by other surgical techniques. Frequently these therapies have required open surgeries with their attendant difficulties.

Devices have been created for inserting closures into a blood vessel or on its exterior that are designed to block the opening and/or soak up fluids that escape the vessel, or are present in the opening through the skin leading to the vessel. Such devices have, however, proven unsatisfactory in many respects, as have therapies for closing naturally-occurring openings in tissue. Needs therefore exist for improved and/or alternative devices and systems for inserting a closure for an opening in tissue that produces a seal without significantly blocking adjacent flow where desired (e.g. through a blood vessel), and fills the opening where that is desirable.

SUMMARY

In certain aspects, the present disclosure provides systems and methods capable of sealing an opening in a bodily wall of a patient. In accordance with some forms, such systems and methods use a resisting member applying a resistive force to an elongated body having a vascular closure device coupled to an end region. In some embodiments, the present disclosure provides an apparatus coupled to a vascular closure device, the apparatus being constructed and arranged to interact with a resisting member comprising a grip portion to apply a force to the vascular closure device to substantially occlude a hole in a vessel wall. The apparatus can include: an elongated body comprising a proximal end region, a distal end region, a high-resistance portion, and a low-resistance portion, with the high-resistance portion positioned adjacent to the proximal end region, the low-resistance portion positioned adjacent to the distal end region, and the distal end region coupled to the vascular closure device. The elongated body is constructed and arranged to slidably couple with and contact the resisting member so as to cause a resistive force between the elongated body and the resisting member.

In some instances, the high-resistance portion is constructed and arranged to interface with the resisting member such that the resistance-resistive force is greater than a conforming force. Additionally, some embodiments disclose the resisting member and the high-resistance portion being constructed and arranged such that the resistive force is less than a deforming force. Some of these arrangements are formed by the high-resistance portion defining a large diameter portion and the low-resistance portion defining a small diameter portion. Furthermore, in some instances, the high-resistance portion defines a plurality of large-diameter portions separated by small-diameter portions along a length of the elongated body.

In some aspects, the present disclosure provides a system arranged to conform a vascular closure device over a hole in a vessel wall to occlude the hole, including an elongated body comprising a proximal end region, a distal end region, a high-resistance portion, and a low-resistance portion. The high-resistance portion may be positioned adjacent to the proximal end region, the low-resistance portion may be positioned adjacent to the distal end region, and the distal end region may be coupled to the vascular closure device. A resisting member including a grip portion is constructed and arranged to slidably couple with and contact the elongated body wherein a resistive force resists longitudinal movement between the elongated body and the resisting member. In some instances, the high-resistance portion defines a large diameter portion and the low-resistance portion defines a small diameter portion. Additionally, the system further comprises a stop member positioned at the proximal end region of the elongated body.

Some embodiments of the present disclosure teach a system arranged to conform a vascular closure device over a hole in a vessel wall to occlude the hole, which includes an elongated body comprising a proximal end region and a distal end region, with the distal end region coupled to the vascular closure device. A resisting member including a grip portion is constructed and arranged to slidably couple with and contact the elongated body. The elongated body and the resisting member interface such that a resistive force resists longitudinal movement between the elongated body and the resisting member. As an example, the resistive force has a maximum static resistive force during a non-sliding condition and a maximum dynamic resistive force during a sliding condition. An operator applies force to the grip portion of the resisting member and the resisting member applies force up to the maximum static resistive force or the maximum dynamic resistive force to the elongated body. The maximum static resistive force is greater than a conforming force sufficient to occlude the hole. In some cases, the maximum dynamic resistive force is greater than a conforming force sufficient to occlude the hole. Additionally, in some embodiments, the maximum static resistive force is less than a deforming force of the vascular closure device.

Further forms, objects, features, aspects, benefits, advantages, and embodiments of the present invention will become apparent from a detailed description and drawings provided herewith.

BRIEF DESCRIPTION OF THE DRAWINGS

FIG. 2 is a cross-sectional view of the system illustrated in FIG. 1.

FIG. 3 is a perspective view of one embodiment of an elongated body and vascular closure device.

FIG. 7 is a side elevational view of an elongated body having spherical protrusions, an end stop, and a vascular closure device coupled to one end.

FIG. 8 is a side elevational view of an elongated body having shoulder protrusions, an end stop, and a vascular closure device coupled to one end.

FIG. 9 is a side elevational view of an elongated body having tapered protrusions, an end stop, and a vascular closure device coupled to one end.

FIG. 10 is a side elevational view of an elongated body having spherical protrusions in abutting contact, an end stop, and a vascular closure device coupled to one end.

FIG. 31 is the system illustrated in FIG. 24 in an eighth position, with the elongated body severed and removed, leaving the vascular closure device in situ.

DESCRIPTION OF THE ILLUSTRATED EMBODIMENTS

Figure 1:
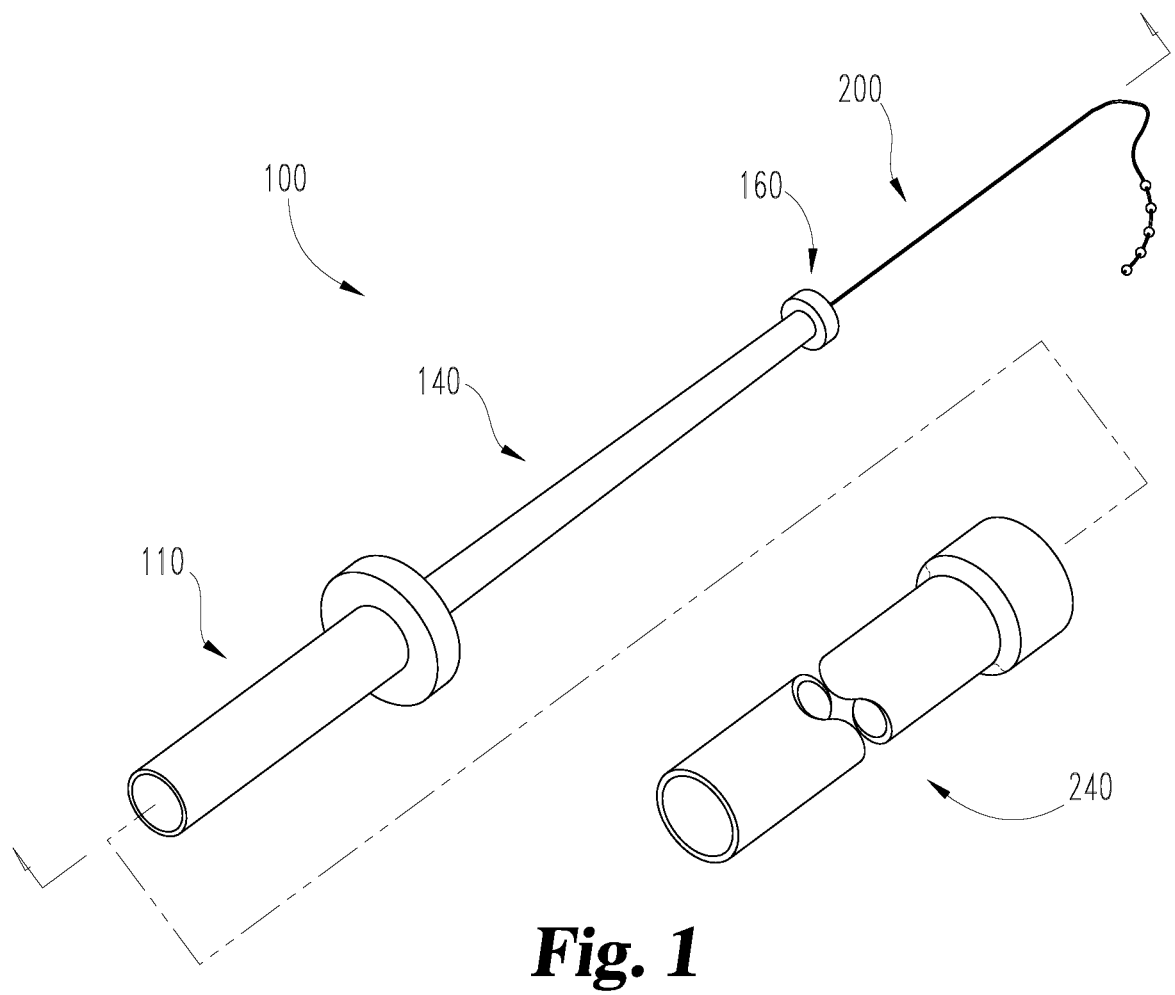
FIG. 1 is a perspective view of an embodiment of a system for closing a hole in a vessel wall.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

With respect to the specification and claims, it should be noted that the singular forms "a", "an", "the", and the like include plural referents unless expressly discussed otherwise. As an illustration, references to "a device" or "the device" include one or more of such devices and equivalents thereof. It also should be noted that directional terms, such as "up", "down", "top", "bottom", and the like, are used herein solely for the convenience of the reader in order to aid in the reader's understanding of the illustrated embodiments, and it is not the intent that the use of these directional terms in any manner limit the described, illustrated, and/or claimed features to a specific direction and/or orientation.

The description below will focus on use in blood vessels of a human or animal, but it will be understood that the structures disclosed herein have application to a number of other vessels or conduits or bodily cavities. Closure or treatment of undesired openings in a variety of tissues can be performed with structures and methodology as disclosed. Examples of other applications include sealing primary and/or secondary openings of a fistula with healing or correction (e.g., filling) of the fistula between the openings. Such fistulae may include vesico-vaginal fistulae, which are abnormal passages between the vagina and bladder.

Referring now to an exemplary embodiment illustrated in FIGS. 1 and 2, a system 100 for closing an opening in a wall of a vessel, conduit or other bodily cavity comprises an introducer 110, an insertion sheath 140, a resisting member 160, an elongated body 200, and, in some instances, a packing member 130, a pushing member 132, and/or an outer sheath 240. The introducer 110 has a proximal end region 112, a distal end region 114 and a wall 116. The wall 116 has an inner surface 118 and an outer surface 120. The inner surface 118 defines a lumen 122 that is constructed and arranged to receive the vascular closure device 230 and/or the insertion sheath 140. In some instances, the inner surface 118 is constructed and arranged to slidably couple with an outer surface 150 of the insertion sheath.

The wall 116 also forms a flange 124 on the outer surface 120 positioned near the proximal end region 112 of the introducer 110. In some embodiments, the flange 124 has a proximal surface 126 and a distal surface 128. The proximal surface 126 is constructed and arranged to limit the distance that the insertion sheath 140 is insertable into the introducer 110.

As illustrated in FIG. 2, the insertion sheath 140 is positionable within the lumen 122 of the introducer 110. The insertion sheath 140 has a proximal end region 142, a distal end region 144, and a wall 146 having an inner surface 148 and an outer surface 150. The inner surface 148 of the wall 146 defines a lumen 152 constructed and arranged to retain the elongated body 200 of the system 100. The outer surface 150 is constructed and arranged to slidably couple with the inner surface 118 of the wall 116 of the introducer 110 so as to allow the insertion sheath 140 to slide within the lumen 122 of the introducer 110.

The wall 146 of the insertion sheath 140 comprises a flange 154 having a proximal surface 156 and a distal surface 158. In some embodiments, the distal surface 158 of the flange 154 is constructed and arranged to contact the proximal surface 126 of the flange 124 of the introducer 110 so as to prevent the insertion sheath 140 from sliding further into the lumen 122 of the introducer 110. The flange 154 may also include a resisting member 160.

The resisting member 160 of the system 100 is constructed and arranged to resist movement, in at least one direction, of the elongated body 200 relative to the resisting member 160. In some instances, the resisting member 160 contacts a surface of the elongated body 200 and provides resistance through physical contact (e.g., friction and/or interfering features). For example, the resisting member 160 has a friction surface constructed and arranged to contact the outer surface of the elongated body 200 and create a frictional resistance to movement of the elongated body 200 relative to the resisting member 160. In some embodiments, the resisting member 160 contacts a surface of the elongated body 200 and applies a resistive force thereto sufficient to conform the vascular closure device 230 to occlude the hole in the vessel wall.

In some embodiments the resisting member 160 is supported by the hand of the operator. Additionally, or alternatively, the resisting member 160 can be a portion of and/or can be coupled to the insertion sheath 140. For example, as illustrated in FIG. 2, the resisting member 160 comprises a valve that is coupled to and positioned on the proximal end region 142 of the insertion sheath 140. Examples of resistive members 160 include but are not limited to cuffs, valves, resistive pads, and channels.

FIG. 3 illustrates an exemplary embodiment of the elongated body 200. The elongated body 200 comprises a proximal end region 202 and a distal end region 204. Coupled to the distal end region 204 of the elongated body 200 is a vascular closure device 230, such as a domed-shaped sealing member 232. In some instances, the elongated body 200 has a high resistance portion 206 and a low resistance portion 208. In some embodiments, the high resistance portion 206 is positioned near the proximal end region 202 and the low resistance portion 208 is positioned between the proximal end region 202 and the distal end region 204 of the elongated body 200. The high resistance portion 206 and/or the low resistance portion 208 are constructed and arranged such that the high resistance portion 206 and resisting member 160, when interfacing with one another, provide a higher resistive force than the low resistance portion 208 and the resisting member 160 do. For example, the high resistance portion 206 has protrusions or bumps and the low resistance portion 208 has a substantially smooth surface.

The high resistance portion 206, low resistance portion 208, and/or the resisting member 160 can be constructed and arranged for a number of purposes. For example, the high resistance portion 206 is constructed and arranged such that upon interaction with the resisting member 160 sufficient force is exerted on the elongated body 200 and the vascular closure device 230 to conform the vascular closure device 230 against the wall of a vessel and close a hole in the vessel wall as described below. In some instances, the high resistance portion 206, low resistance portion 208, and/or resisting member 160 be constructed and arranged to provide feedback to the operator. For example, the high resistance portion 206 and/or low resistance portion 208 comprise features that provide a tactile feedback and/or an audible feedback through the resisting member 160 to the operator that he/she is applying sufficient force through the resisting member 160 and the elongated body 200 to properly conform the vascular closure device 230 to the vessel wall. The system 100 may also provide feedback regarding the relative movement between the elongated body 200 and the sheath 140. Similarly, in some embodiments, the high resistance portion 206 and/or the resisting member 160 are constructed and arranged so as to provide an indication to the operator that the resisting member 160 is nearing the end of the elongated body 200.

In some instances, the high resistance portion 206 of the elongated body 200 comprises portions having a greater diameter and/or cross-sectional area than other portions of the elongated body 200. For example, the high resistance portion 206 includes protrusions 210. In some embodiments, the protrusions 210 increase the resistance to movement of resisting member 160 relative to the elongated body 200. This increased resistive force increases the force that is transferred from the resisting member 160 to the elongated body 200 through the contact of the resisting member 160 and the elongated body 200. Therefore, the resisting member 160 exerts a greater force to the elongated body 200 and subsequently to the vascular closure device 230.

In some embodiments, the high resistance portion 206 of the elongated body 200 has portions that cause a greater frictional resistance to movement of the resisting member 160 along a length of the elongated body 200 than other portions. For example, the high resistance portion 206 has portions with a greater frictional resistance than the low resistance portion 208. Furthermore, in some instances, the frictional resistance to sliding movement of the resisting member 160 along the surface of the high resistance portion 206 and/or the low resistance portion 208 is greater than a conforming force, so as to conform the vascular closure device 230 to the wall of a vessel and close a hole in the vessel wall.

Various arrangements for varying the frictional resistance along a length of the elongated body 200 are contemplated. For example, the surface roughness of one portion may be coarser than the surface roughness of another portion (e.g., one portion may have an average surface roughness ($R_a$) of 25 micrometers or more with other portions having an $R_a$ of 0.4 micrometers or less). Similarly, portions may have a different lay (such as different directions in directional lay and/or directional lay and random lay), different waviness, and/or different surface integrity, to name a few non-limiting examples. As will be appreciated, other arrangements may be used to vary the frictional resistance along a length of the elongated body, such as lubricating some portions of the elongated body 200 and leaving other portions dry.

As shown in FIGS. 2 and 24-31, the elongated body 200 may include a locking member 222 positioned near the distal end region 204. The locking member 222 may be constructed and arranged to secure a second vascular closure device positioned against the outer surface 1012 of the vessel wall 1008 (opposite of the first vascular closure device 230) and/or to secure a packing member 130 in and/or around the hole 2016 in the vessel wall. In many embodiments, a locking member 222 is constructed and arranged so as to be capable of sustaining a conforming force between the first vascular closure device 230 and the second vascular closure device and/or the packing member 130.

Figure 4:
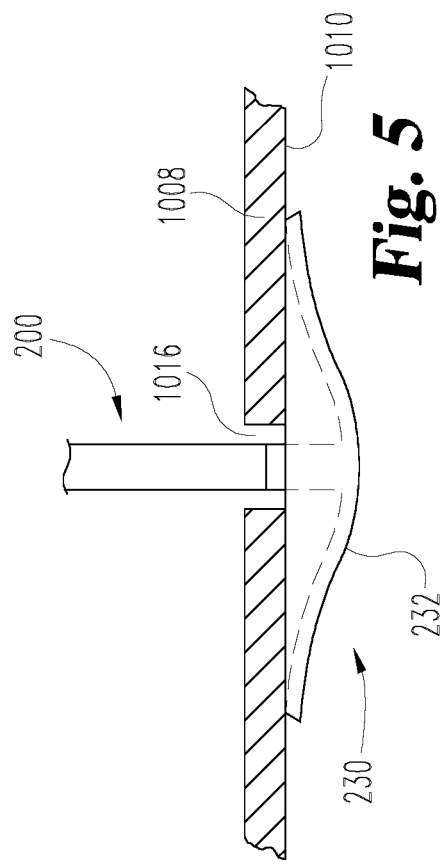
FIG. 4 is a cross-sectional side view of one embodiment of a vascular closure device coupled to an elongated body and in an unconformed configuration.
Figure 5:
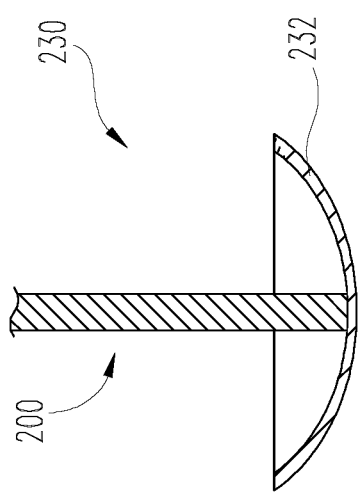
FIG. 5 is a side elevational view of the vascular closure device of FIG. 4 under a conforming force.
Figure 6:
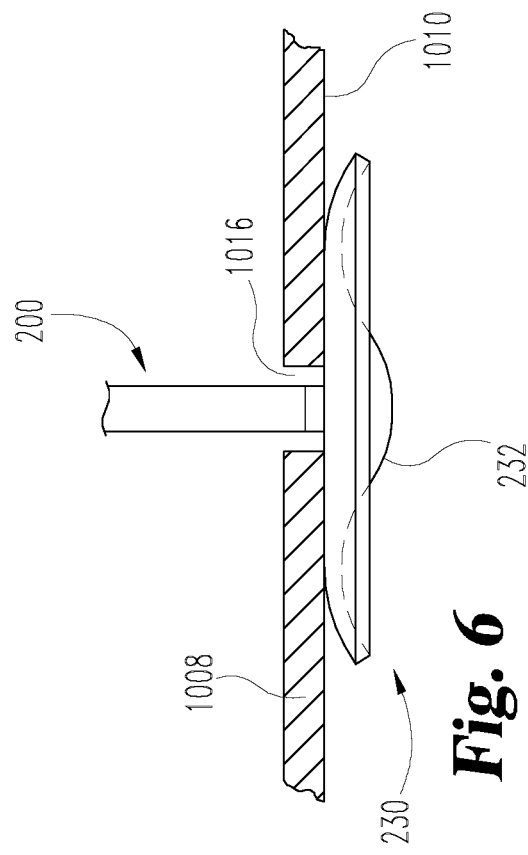
FIG. 6 is a side elevational view of the vascular closure device of FIG. 4 under a deforming force.

The elongated body 200 coupled to the vascular closure device 230 is constructed and arranged so as to be capable of applying a conforming force to the vascular closure device 230. The conforming force is the amount of force necessary to conform the vascular closure device 230 to the inner surface 1010 of the vessel wall 1008, such that the vascular closure device 230 substantially occludes the hole 1016 in the vessel wall 1008 and substantially seals the hole 1016 to prevent or substantially reduce any blood from escaping the vessel 1006. Illustrated in FIG. 4 is an exemplary vascular closure device 230 in an unstressed configuration. As a conforming force is applied to the vascular closure device 230 by the elongated body 200, the vascular closure device 230 deforms into a conforming configuration, as illustrated in FIGS. 5 and 6. FIGS. 5 and 6 illustrate varying ranges of deformation that may be applied to vascular closure device 230 while substantially sealing hole 1016. It should be understood that FIGS. 4-6 show exaggerated forms of vascular closure device 230 for illustrative purposes. Vascular closure devices may be used with different shapes as appropriate for particular applications.

A force that is greater than the conforming force can be applied to the vascular closure device 230 through the elongated body 200. In some instances, a distorting force is applied, which is the lesser of the amount of force necessary to deform the vascular closure device 230 beyond a shape that occludes the hole 1016 in the vessel wall 1008, the amount of force necessary to pull the vascular closure device 230 through the hole 1016 in the vessel wall 1008, and/or the amount of force necessary to damage the vascular closure device 230 and/or the vessel wall 1008.

The vascular closure device 230 may be any implement used to cover and occlude a hole 1016 in a vessel wall. As will be apparent to one of ordinary skill in the art, a variety of vascular closure devices 230 may be used with the disclosed systems. For example, a domed-shaped sealing member 232 having a semi-elliptical shape in an unstressed configuration may be used. As will be appreciated by one of ordinary skill in the art, vascular closure devices 230 may have different shapes, different dimensions, different materials, and/or different properties. For example, a system 100 may be constructed and arranged to position and conform a vascular closure device 230 that may be left in situ after the procedure.

FIGS. 7-13 illustrate various embodiments of the elongated body 200. As illustrated in FIG. 7, the elongated body 200 comprises ribs and/or protrusions 210 located in the proximal end region 202 of the elongated body 200. The ribs and/or protrusions 210 can be of a variety of shapes, including barbs, knots, frusto-conical segments, or flat surfaces, to name a few non-limiting examples. Additionally, the ribs and/or protrusions 210 may be made monolithically with the elongated body 200 or separate from the elongated body 200 and attached to it later.

In some instances, the protrusions 210 comprise a series of spheres 212 spaced along the length of the proximal end region 202 of the elongated body 200. As illustrated in FIG. 8, the protrusions 210 comprise a series of shoulders 214 spaced along the length of a portion of the elongated body 200. In some embodiments, the protrusions 210 include tapered portions such as wedges 216 that have a greater resistive force moving in a direction along the length of the elongated body 200 than in another direction. For example, as shown in FIG. 9, the wedges 216 provide a greater resistive force to movement of the resisting member 160 in a proximal to distal direction along a length of the elongated body 200 than the resisting member 160 moving in a distal to proximal direction. This may be accomplished, for example, by one or more sides of a protrusion 210 having a sloped and/or slanted portion.

The ribs and/or protrusions 210 are spaced serially along a length of the elongated body 200 and/or in abutting contact. For example, the protrusions 210 are spaced with portions of lower resistance positioned between the higher resistance protrusions 210. The spacing may be even or uneven and, in some instances, may increase or decrease in length along a proximal-to-distal direction or vice-versa.

Figure 11:
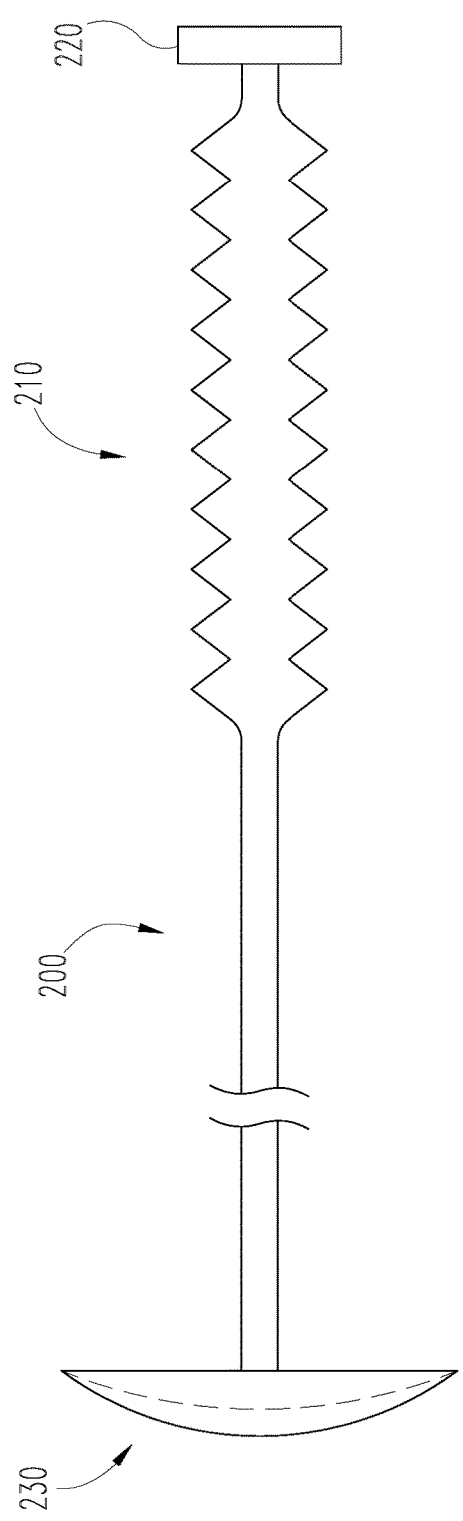
FIG. 11 is a side elevational view of an elongated body having a long protrusion with an irregular outer surface, an end stop, and a vascular closure device coupled to one end.

In some embodiments, the ribs or protrusions 210 are in abutting contact such that the diameter of the elongated body 200 between the protrusions 210 is greater than the diameter of the elongated body 200 in the low resistance portion 208 (See FIG. 10). In some instances, a series of protrusions 210 are combined together and/or one long protrusion 210 exists along a length of the elongated body 200, as illustrated in FIG. 11. In some situations, a protrusion 210 has an irregular outer surface arranged to vary the resistive force exerted to the resisting member 160, as the resisting member 160 travels along the surface of the protrusion 210.

Figure 12:
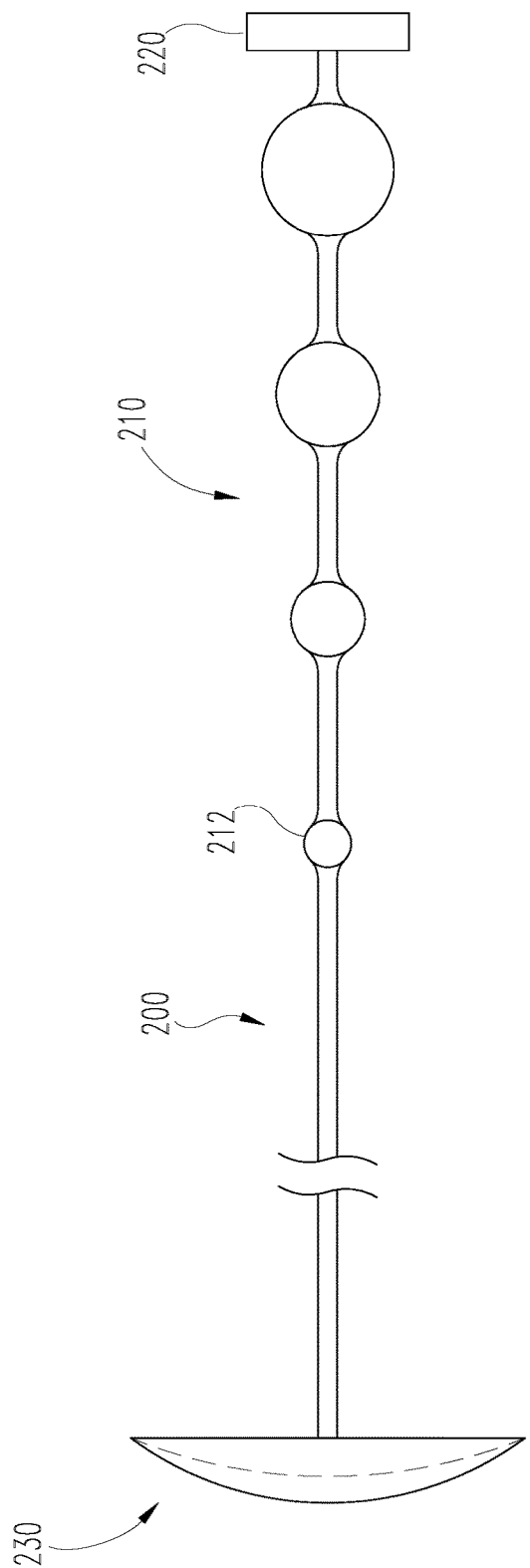
FIG. 12 is a side elevational view of an elongated body having spherical protrusions increasing in diameter, an end stop, and a vascular closure device coupled to one end.
Figure 13:
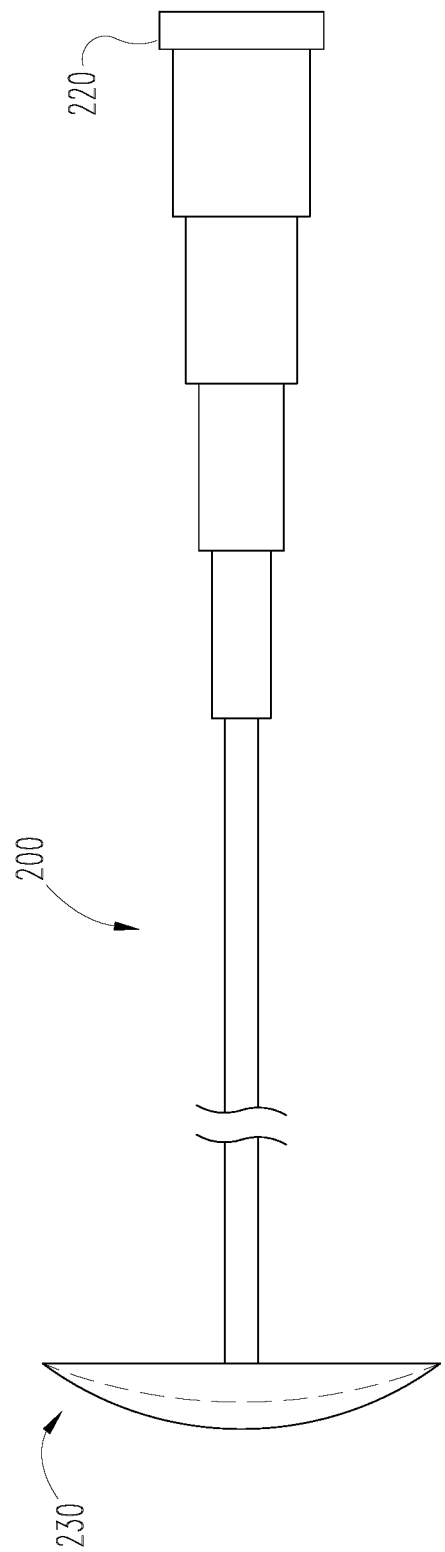
FIG. 13 is a side elevational view of an elongated body having a series of abutting shoulder protrusions increasing in diameter, an end stop, and a vascular closure device coupled to one end.

In some instances, individual and/or serial protrusions 210 increase or decrease in size, such as diameter, in a direction along a length of a portion of the elongated body 200. For instance, as shown in FIG. 12, the spheres 212 of the elongated body 200 increase in diameter as one moves proximally along the length of the elongated body 200 and nearing the end of the elongated body 200 in the proximal end region 202. FIG. 13 illustrates an elongated body 200 having a series of abutting shoulder protrusions that increase in diameter. Additionally, in some embodiments, the elongated body 200 may optionally include an end stop 220 constructed and arranged to prevent the removal of the resisting member over the end of the elongated body 200.

Figure 14:
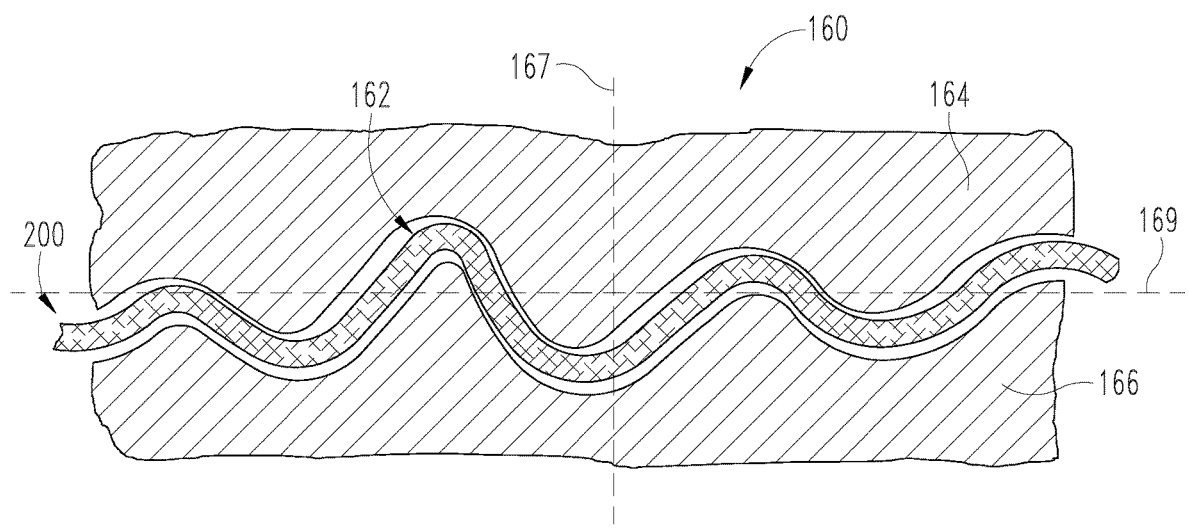
FIG. 14 is a cross-sectional view of an elongated body extending through a tortuous channel of a resisting member; the tortuous channel changing directions along a vertical axis.
Figure 15:
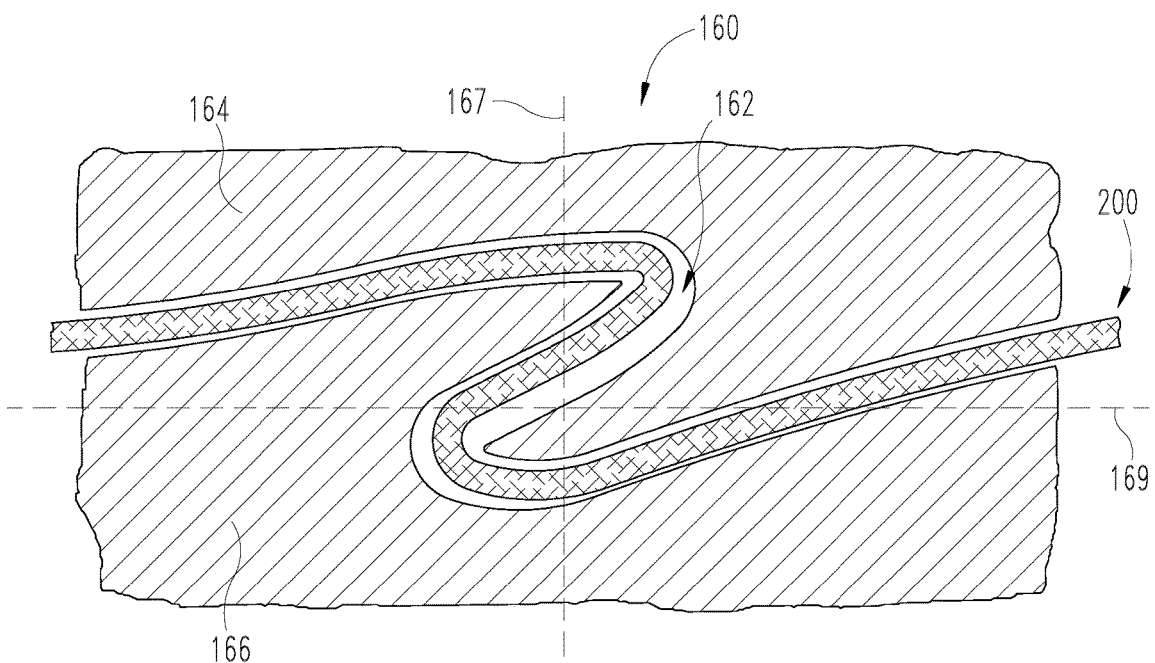
FIG. 15 is a cross-sectional view of an elongated body extending through a tortuous channel of a resisting member; the tortuous channel changing directions along both a vertical and horizontal axis.

FIGS. 14-21 illustrate various exemplary embodiments of the resisting member 160 of the system 100. As illustrated in FIGS. 14 and 15, the resisting member 160 comprises a first block 164 and a second block 166 that cooperate to define a tortuous path for the elongated body 200, such as a channel 162.

In some embodiments, the tortuous path changes direction along a single axis and/or along more than one axis in the resisting member 160. For example, as illustrated in FIG. 14, the channel 162 defined by the resisting member 160 extends continuously in a direction along a horizontal axis 169 and changing directions only along a vertical axis 167. Alternatively, the channel 162 may change directions along both the horizontal axis 169 and the vertical axis 167 as it extends through the resisting member 160, as illustrated in FIG. 15.

The shape and size of the tortuous path may be constructed and arranged by changing the shapes of the surfaces of the first block 164 and/or the second block 166 and/or by changing the orientation of the first block 164 relative to the second block 166. For instance, the first block 164 and the second block 166, as illustrated in FIG. 14, may be moved towards one another along the vertical axis 167 so as to decrease the size of the channel 162 and further constrain the elongated body 200 within the resisting member 160. Alternatively, or in addition, the first block 164 and the second block 166 may be moved in opposite directions along the horizontal axis 169 so as to decrease the size of only some portions of the channel 162. The first block 164 and second block 166 may be attached together, held immovable with respect to each other, or constructed of a single piece.

Figure 16:
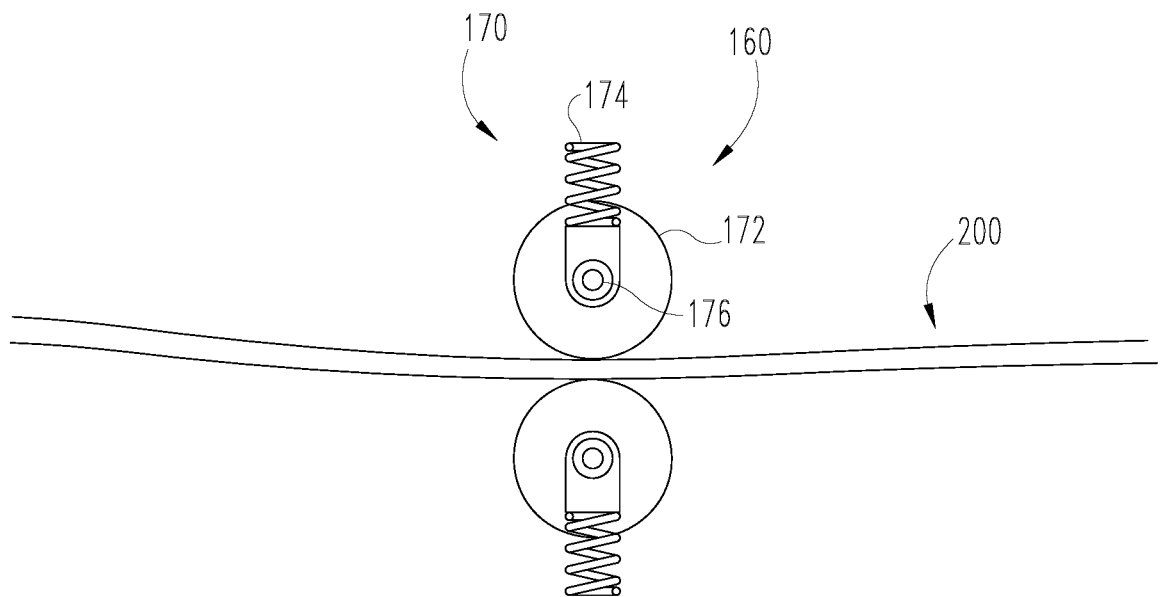
FIG. 16 is a side elevational view of a resisting member having a rolling resistance system.

FIG. 16 illustrates one embodiment of the resisting member 160 comprising a rolling resistance system 170 having one or more rolling members 172, a spring 174, and/or an axle 176. The rolling members 172 are positioned around the axle 176 and constructed and arranged to rotate. In some embodiments, the spring 174 pushes on the axle 176 extending through the roller member 172 so as to force the rolling member 172 against the elongated body 200. In some instances, this force increases the rolling resistance of the roller member 172 against the surface of the elongated body 200 and, therefore, increases the resistance to relative movement. In some embodiments, the spring 174 comprises a torsion member and/or a breaking element coupled to the axle 176 and/or the roller members 172. For example, the torsion member may be constructed and arranged to resist the rotation of the rolling member 172. This may be accomplished by coupling the torsion member to the rolling member 172 such that rotation of the rolling member 172 would twist the torsion member. Advantageously, in some cases, the resistive force exerted by the torsion member would be variable, for example, such as by increasing the resistive force as the rolling member 172 twists the torsion member.

Figure 17:
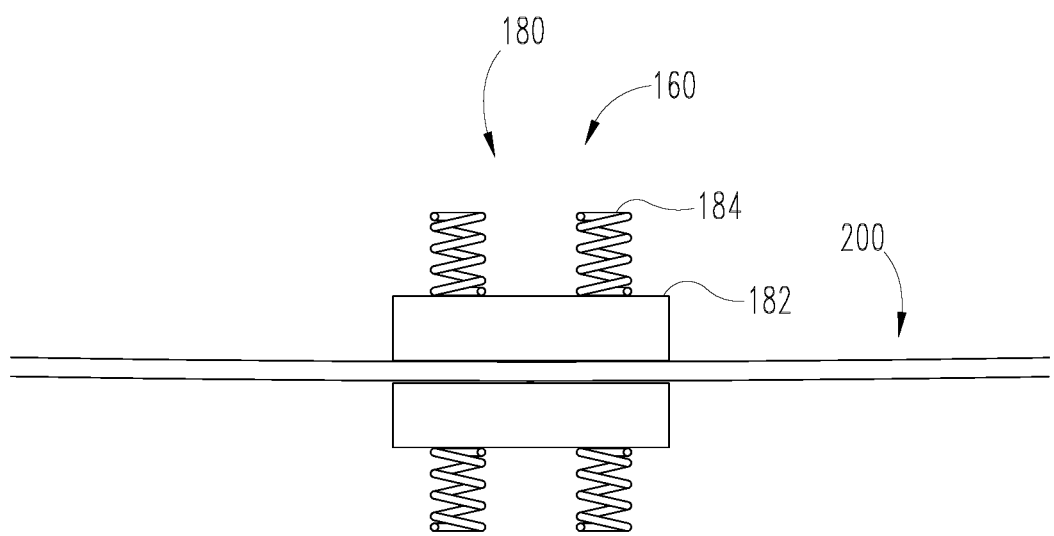
FIG. 17 is a side elevational view of a resisting member having a brake pad system.

FIG. 17 illustrates an alternative embodiment of the resisting member 160 comprising a brake pad system 180. The brake pad system 180 comprising one or more brake pads 182, and in some embodiments, one or more springs 184. The brake pads 182 frictionally contact the surface of the elongated body 200 so as to frictionally resist movement of the elongated body 200 relative to the brake pads 182. The springs 184 increase the contact force of the brake pad 182 to the surface of the elongated body 200 so as to increase the resistive force between the brake pad 182 and the elongated body 200.

Figure 18:
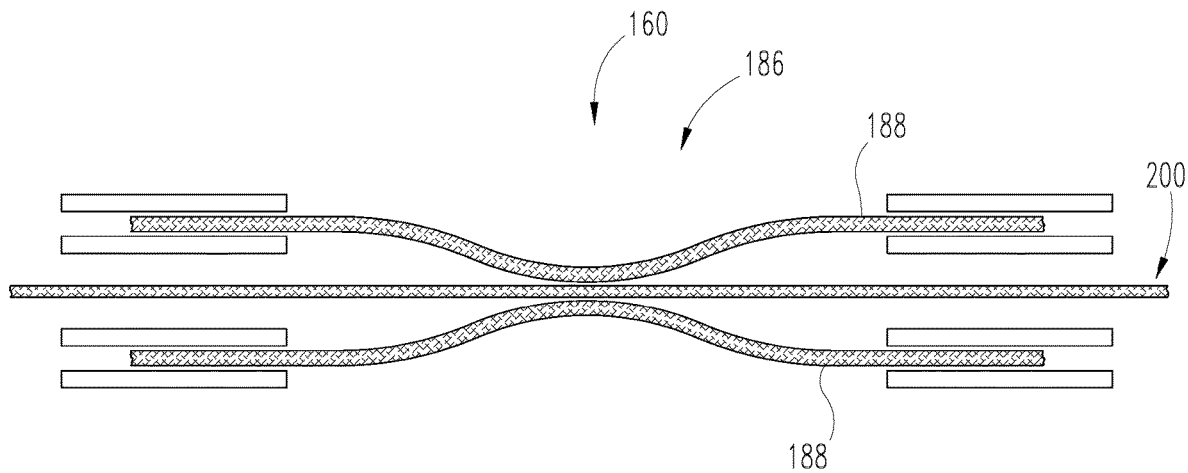
FIG. 18 is a side elevational view of a resisting member having a leaf spring system.

FIG. 18 illustrates a leaf spring system 186 embodiment of a resisting member 160. The leaf spring system 186 comprises one or more leaf springs 188 that contact the surface of the elongated body 200 and cause a frictional resistance to motion of the elongated body 200 relative to the leaf spring system 186.

Figure 19:
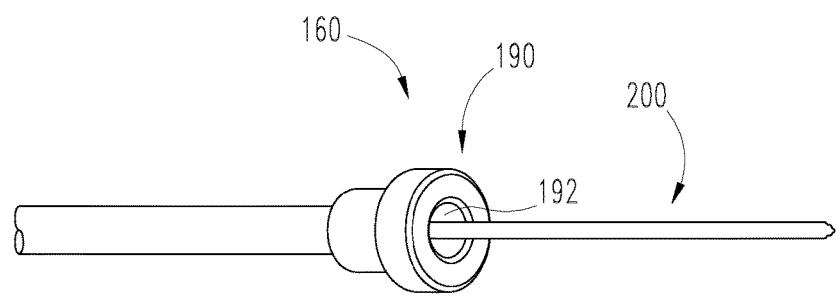
FIG. 19 is a side elevational view of a valve-type resisting member.

FIG. 19 illustrates an embodiment of the resisting member 160 comprising a valve 190. In some instances, the valve 190 comprises a sealing member 192 within the valve that frictionally contacts the surface of the elongated body 200. In some embodiments, the valve 190 may comprise a hemostasis valve, such as a tuohy-borst valve, with the sealing member 192 in the valve 190 being adjustable.

Figure 20:
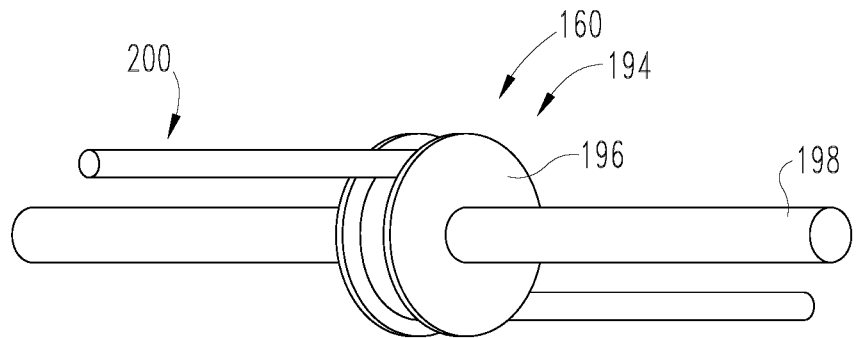
FIG. 20 is a perspective view of a belt friction system and/or a pulley system of a resisting member.
Figure 21:
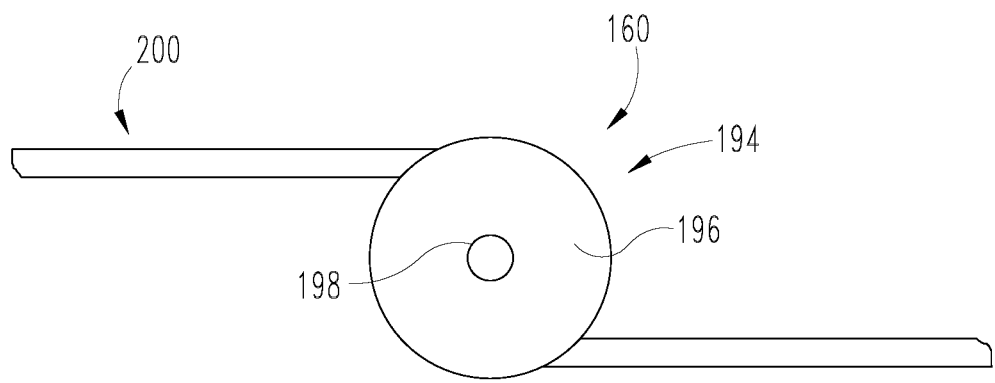
FIG. 21 is a side elevational view of the system illustrated in FIG. 20.

FIGS. 20 and 21 illustrate embodiments such as a belt friction system and/or a pulley system of the resisting member 160. In some instances, the system 194 comprises an elongated body 200 wrapped around a cylinder 196 that is fixedly coupled to an axle 198. As one end of the elongated body 200 is pulled, only part of the force is transmitted to the other end due to the friction between the surface of the elongated body 200 and the cylinder 196. The elongated body 200 is wrapped around the cylinder 196 one or more times, depending on the amount of force desired to be transmitted to the other portion of the elongated body 200 and/or the amount of force necessary to initiate a slipping condition between the elongated body 200 and the cylinder 196. For example, if the operator desires more resistive force before the elongated body 200 begins to slip on the cylinder 196, the operator may wrap the elongated body 200 around the cylinder 196 more times.

Alternatively, the cylinder 196 may be fixedly coupled to a torsion member and rotationally coupled to the axle 198, similar to that discussed with regards to the embodiment illustrated in FIG. 16. In some instances, as the elongated body 200 rotates the cylinder 196 around the axle 198, the torsion member is twisted and resists additional twisting and rotation of the cylinder 196.

In some embodiments, the resisting member 160 is integrated into a portion of the system 100 such as the insertion sheath 140, introducer 110, and/or the outer sheath 240. In other instances, the resisting member 160 is a separate component such as a sheath that an operator grips and slides along a length of a portion of the elongated body 200. In several embodiments, the resisting member 160 comprises a grip portion and is constructed and arranged to slidably couple with and contact a surface of the elongated body 200 wherein a resistive force resists longitudinal movement between the elongated body 200 and the resisting member 160.

In some instances, the elongated body 200 and the resisting member 160 are constructed and arranged to generate specific resistive forces in static and/or dynamic (e.g., sliding) conditions. For example, the maximum resistive force may be selected so as to be less than the deforming force of the vascular closure device 230 and/or greater than the conforming force of the vascular closure device 230 for when the elongated body 200 and resisting member 160 are in a static condition (e.g., not sliding). Similarly, the maximum resistive force during a dynamic condition may be selected to be less than the deforming force of the vascular closure device 230 and/or greater than the conforming force.

In some instances, the static resistive force and/or the dynamic resistive force may be variable. For instance, the static resistive force and/or the dynamic resistive force may be variable along a length of a portion of the elongated body 200. Alternatively, or additionally, the interface between the resisting member 160 and the elongated body 200 may be arranged such that the static resistive force and/or the dynamic resistive force are selectively variable by an operator such that the operator may increase and/or decrease the resistive force in static and/or dynamic conditions so as to achieve the desired force on the vascular closure device 230.

Figure 22:
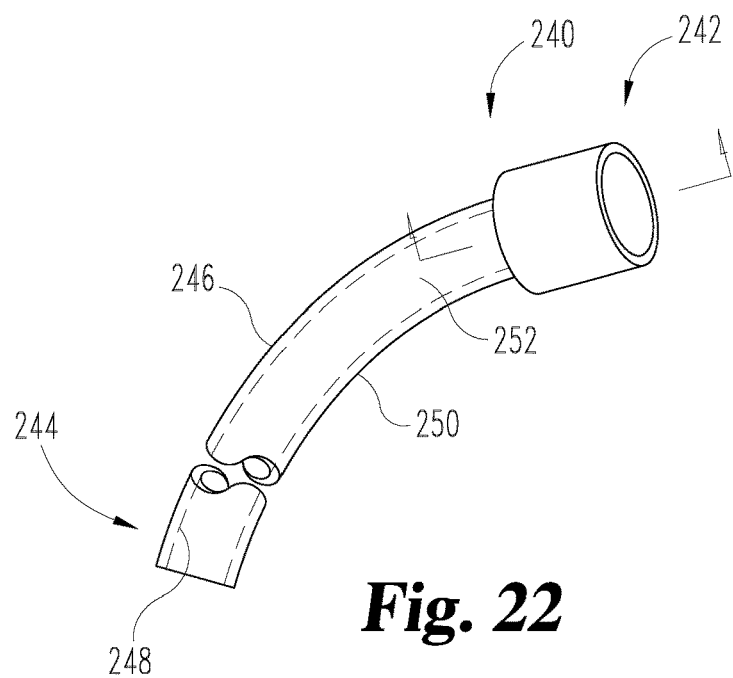
FIG. 22 is a perspective view of one embodiment of an outer sheath.
Figure 23:
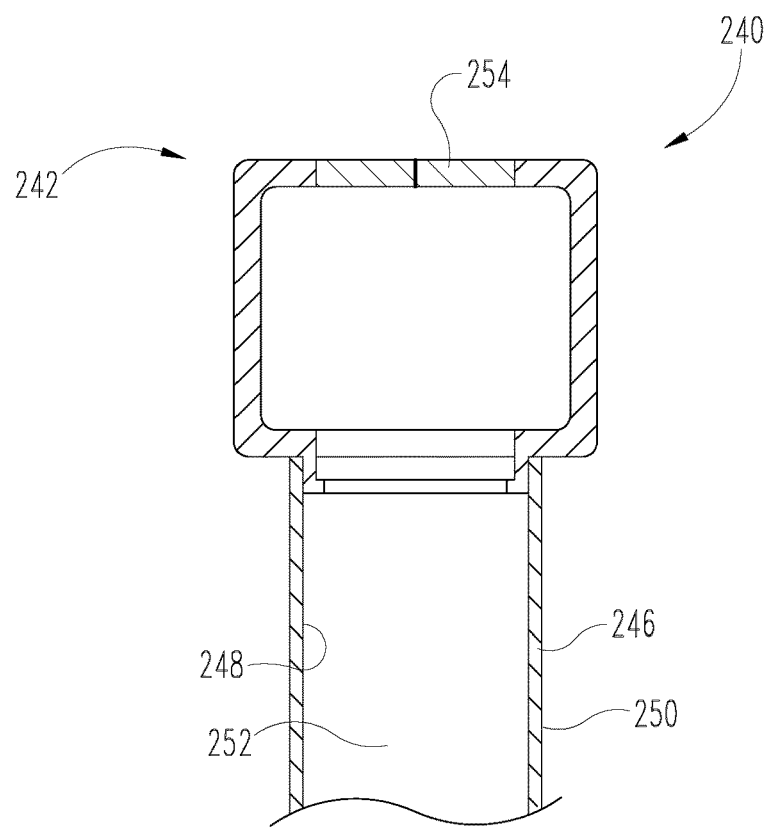
FIG. 23 is a cross-sectional view of one embodiment of an outer sheath.

FIGS. 22 and 23 illustrate an embodiment of the outer sheath 240 that may be included in the system 100 or outer sheath 240 may be a third party catheter introducer, for example. The outer sheath 240 comprises a proximal end region 242, a distal end region 244 and a wall 264 having an inner surface 248 and an outer surface 250. The inner surface 248 defines a lumen 252 arranged to receive the introducer 110, insertion sheath 140, and/or the vascular closing device 230. In some instances, the outer sheath 240 comprises a seal member 254, such as a hemostasis valve, positioned in the proximal end region 242. In some embodiments, seal member 254 is used as the resisting member 160.

In some embodiments, the system 100 includes a packing member 130, a pushing member 132, and a locking member 222. The packing member 130 may be positioned within the insertion sheath 140 proximal to the vascular closure device 230, and is coupled to the elongated body 200. In some embodiments, such as those illustrated in FIGS. 2 and 24-31, the packing member 130 and locking member 222 are slidably coupled to the elongated body 200 and pushing member 132 is arranged to push the locking member 222 against the packing member 130 to pack the packing member 130 against the outer surface 1012 of the vessel wall 1008.

In the embodiments having a locking member 222, the locking member 222 may retain the packing member 130 in position against the vessel wall 1008. For example, the locking member 222 may couple to a portion of the elongated body 200 in the distal end region 204 and apply a compressive force to the packing member 130. In some instances, the locking member 222 may be retained by a protrusion 224 in the distal end region 204 of the elongated body 200. As the packing member 130 is positioned adjacent to the outer surface 1012 of the vessel wall 1008 by the pushing force of the pushing member 132, the locking member 222 may contact a portion of the packing member 130 and resist movement of the packing member 130 away from the vessel wall 1008. Similarly, the system 100 may be constructed and arranged such that the force that the packing member 130 exerts on the locking member 222 is communicated to the vascular closure device 230 through the elongated body 200 and retains the vascular closure device 230 in a conformed configuration.

The above mentioned components may be made using materials and methods apparent to one of ordinary skill in the art. For example, the elongated body 200, vascular closure device 230, and/or packing member 130 can be made of any material suitable for implantation within the body of the patient. Appropriate materials include synthetic materials and a grown or harvested tissue, such as an extracellular matrix material (ECM) such as porcine small intestinal submucosa (SIS). In some instances, spongy or foam materials or other forms of materials are used. Preparation of such materials is disclosed in U.S. patent application Ser. No. 12/489,199 (filed Jun. 22, 2009 and incorporated herein by reference in its entirety).

As noted above, in particular embodiments the material is a collagenous extracellular matrix material such as SIS, and it is treated to partially denature and expand the native collagenous structure, for example with sodium hydroxide, to provide desired porosity and/or foam characteristics when dried. In certain embodiments, the extracellular matrix material can be processed to be medically acceptable while retaining a native collagenous microarchitecture (e.g. a native sheet form) and endogenous bioactive substances from an animal source tissue, such as a porcine, ovine, bovine or equine source tissue. Such endogenous substances can for example include one, some, or all of growth factors (e.g., Fibroblast Growth Factor-2), glycosaminoglycans, and proteoglycans. The extracellular matrix material can be treated with a chemical crosslinking agent, for example glutaraldehyde or a carbodiimide, to add crosslinks over and above any native crosslinks present, or can lack any such treatment. In other embodiments, the elongated body 200, vascular closure device 230, and/or packing member 130 can comprise a reconstituted collagen sheet or foam, optionally crosslinked with a chemical crosslinker such as those discussed above.

The portions of the system 100 that are not implanted into the body of the patient may be made of any number of materials. For example, the introducer 110, pushing member 132, insertion sheath 140, resisting member 160, and/or outer sheath 240 may be made of plastic or other suitable material. In some instances the material may need to maintain its rigidity over a sufficient length (e.g., 10 to 20 cm or more), so that an operator may manipulate a proximal portion and impart movement of a distal portion, such as with pushing the pushing member 132. For example, when pushing the packing member 130 with the pushing member 132, the operator can manipulate such longer embodiments of the pushing member 132 from outside of the patient, with tactile feedback indicated passage of the packing member 130 and/or the locking member 222 past the protrusion 224 of the elongated body 200.

Variations of the above described embodiments, as will be apparent to one of ordinary skill in the art, are contemplated by the present disclosure.

Methods of Use

One method of use of system 100 will now be described with respect to closing and repairing an opening in a wall of a blood vessel. As noted previously, it is to be understood that similar usages can be made in other body tissues (e.g., bile or other ducts), or other vessels, conduits or walls. For example, in use with fistulae (e.g., vescio-vaginal fistula), seal(s) as described herein may be placed and held over fistula openings and against tissue substantially as described below, with packing members within the fistula to assist with healing or correction of the fistula.

Reference to the following exemplary method of use will be made with regard to a vessel 1006 positioned beneath tissue 1000 such as skin 1002 and/or muscle/fat 1004 of the body of a patient. The vessel 1006 comprises a vessel wall 1008 having an inner surface 1010, an outer surface 1012, and the inner surface defining a lumen 1014 extending through the vessel 1006.

A surgeon or other medical professional performs and completes desired procedure(s) that involve access to the blood vessel 1006 through hole 1016 in wall 1008 (e.g., balloon catheterization or stenting procedures). If a sheath, cannula or other access device or portal was used for the procedure(s), it can be left in the vessel 1006, and the system 100 described above may be inserted through it. If no such access device is present, or if a change of access device is necessary or desired, outer sheath 240 is placed in the opening by using a dilator with an introducer sheath so that the distal end 244 is inside the vessel 1006. Seal member 254 may provide a barrier preventing blood from exiting the lumen 252 of the outer sheath 240 from the proximal end region 242.

Figure 24:
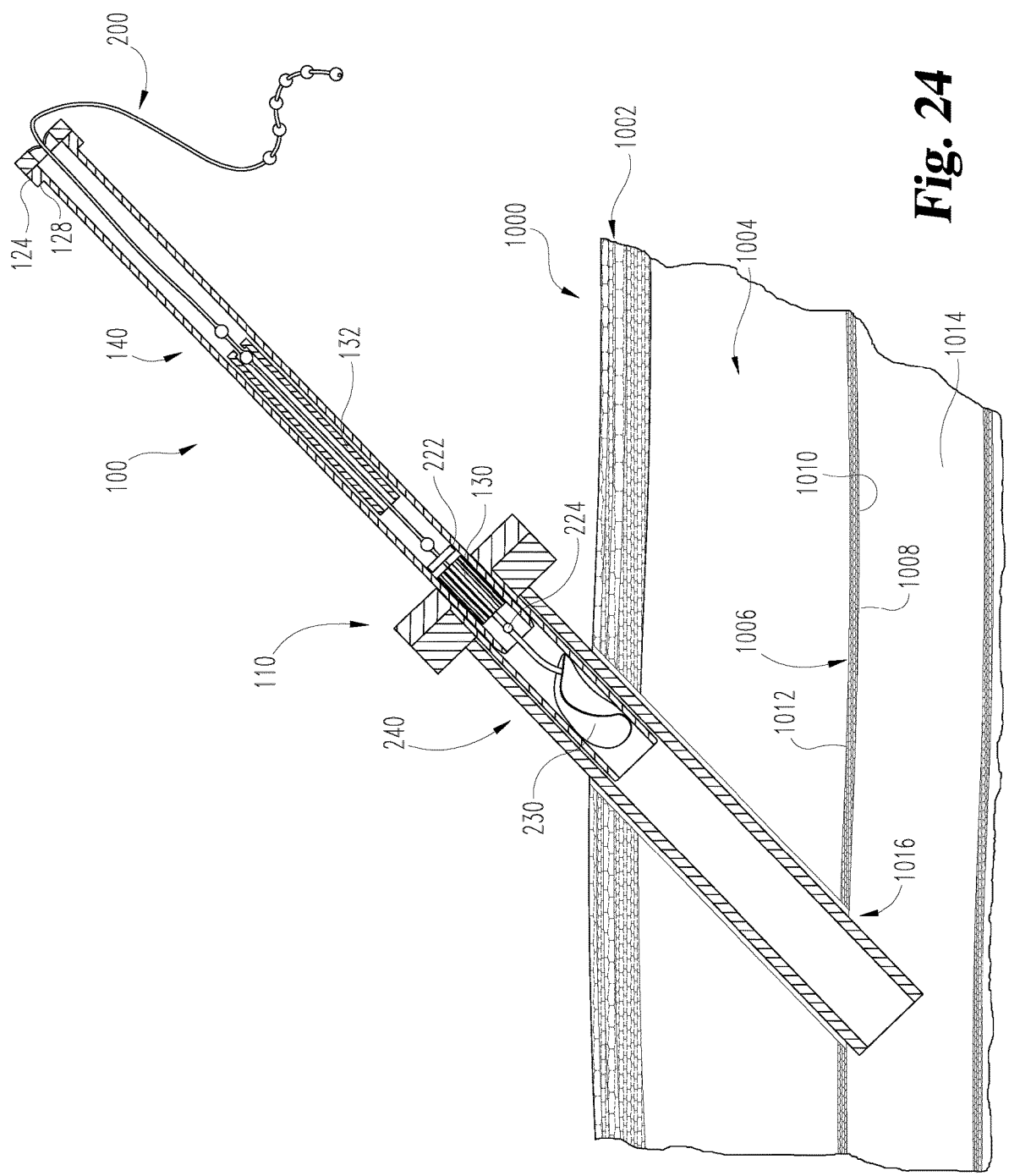
FIG. 24 is a cross-sectional view of a system for closing a hole in a vessel wall in a first position, with the introducer inserted into the outer sheath.
Figure 25:
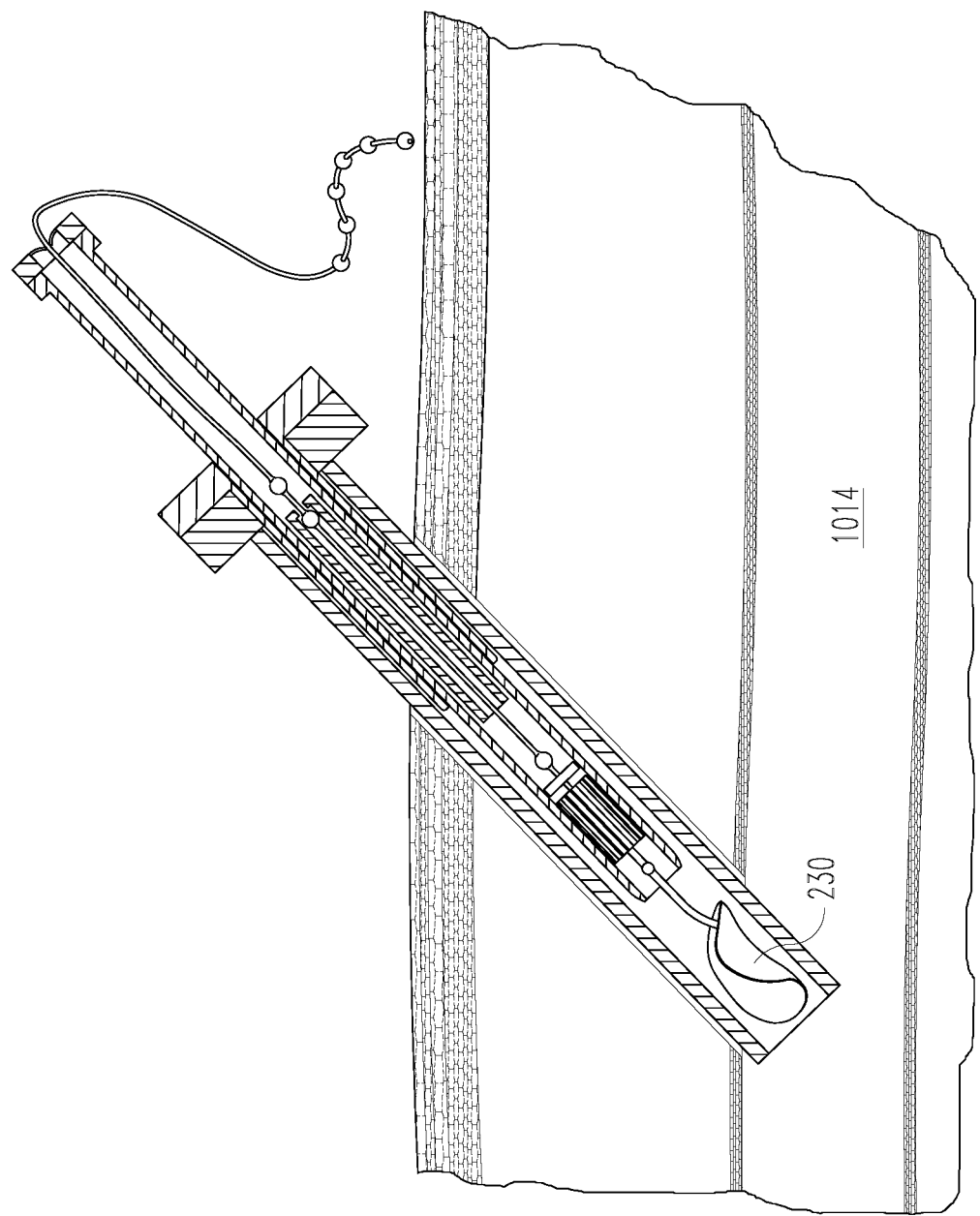
FIG. 25 is the system illustrated in FIG. 24 in a second position, with the vascular closure device and insertion sheath advanced through the introducer.
Figure 26:
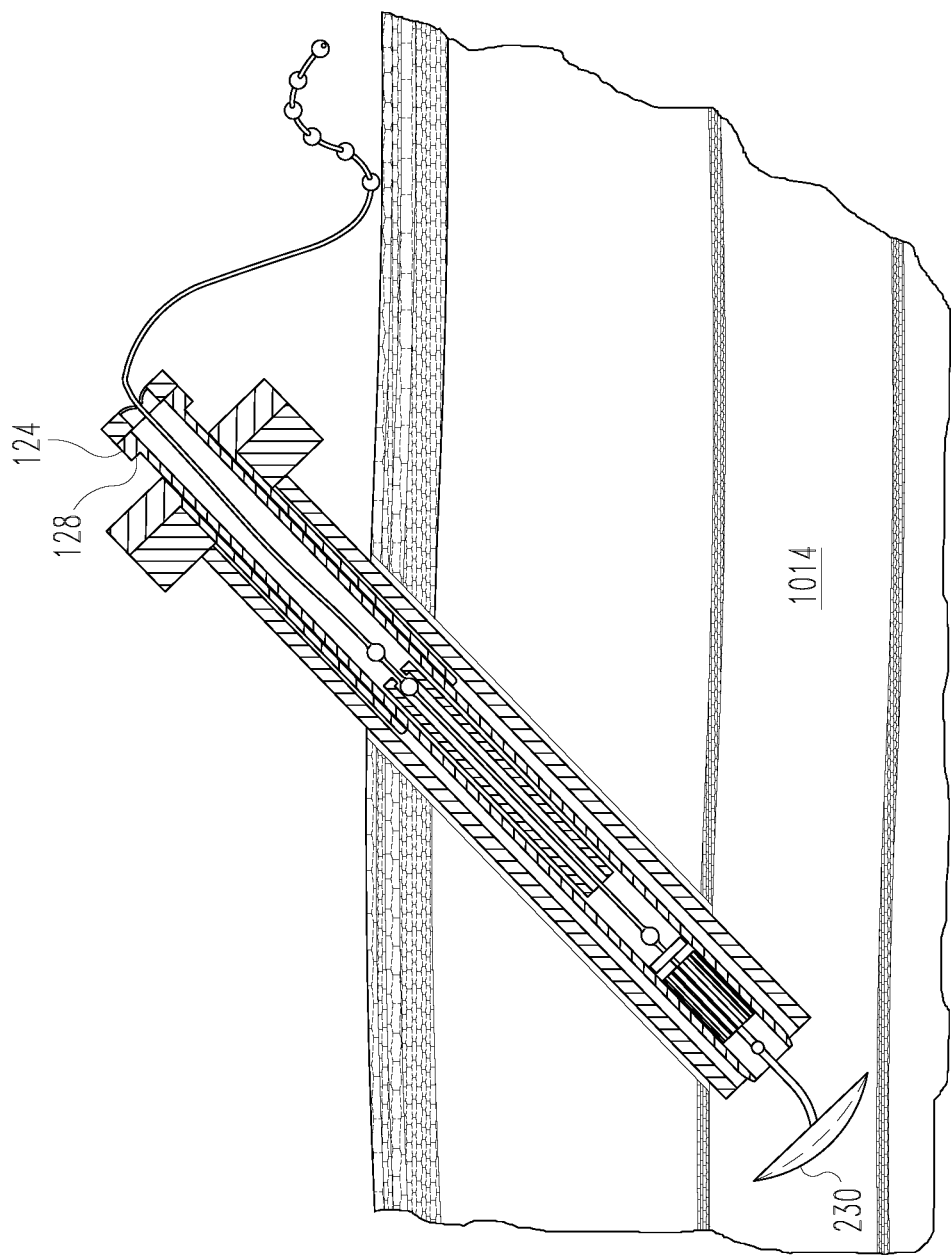
FIG. 26 is the system illustrated in FIG. 24 in a third position, with the vascular closure device advanced into the lumen of the vessel.

As illustrated in FIG. 24, after access is gained to the lumen 1014 of the vessel 1006 within the body of the patient and the vessel 1006 has been used to provide therapy and/or for diagnostic purposes, the system 100, prepared as noted above, is inserted into the lumen 252 of the outer sheath 240 and advanced towards the vessel 1006. As the outer surface 120 of the introducer 110 slides along the inner surface 248 defining the lumen 252, the distal surface 128 of the flange 124 of the introducer 110 contacts a portion of the proximal end region 242 of the outer sheath 240 and prevents further insertion of the introducer 110 within the lumen 252 of the outer sheath 240 (FIG. 24).

If the introducer 110 is shorter in length than the outer sheath 240, the insertion sheath 140, the elongated body 200 and the vascular closure device are advanced through the lumen 122 of the introducer 110 so as to position the vascular closure device 230 and/or portions of the insertion sheath 140 and/or the elongated body 200 within the lumen 252 of the outer sheath 240. The insertion sheath 140 is advanced further so as to position the vascular closure device 230 within the lumen 1014 of the vessel 1006, allowing the vascular closure device 230 to expand into an expanded configuration within the lumen 1014 (see FIG. 26). After the vascular closure device 230 has expanded into an expanded configuration, the resisting member 160, elongated body 200, insertion sheath 140, introducer 110, and/or outer sheath 240 are/is be withdrawn.

Figure 27:
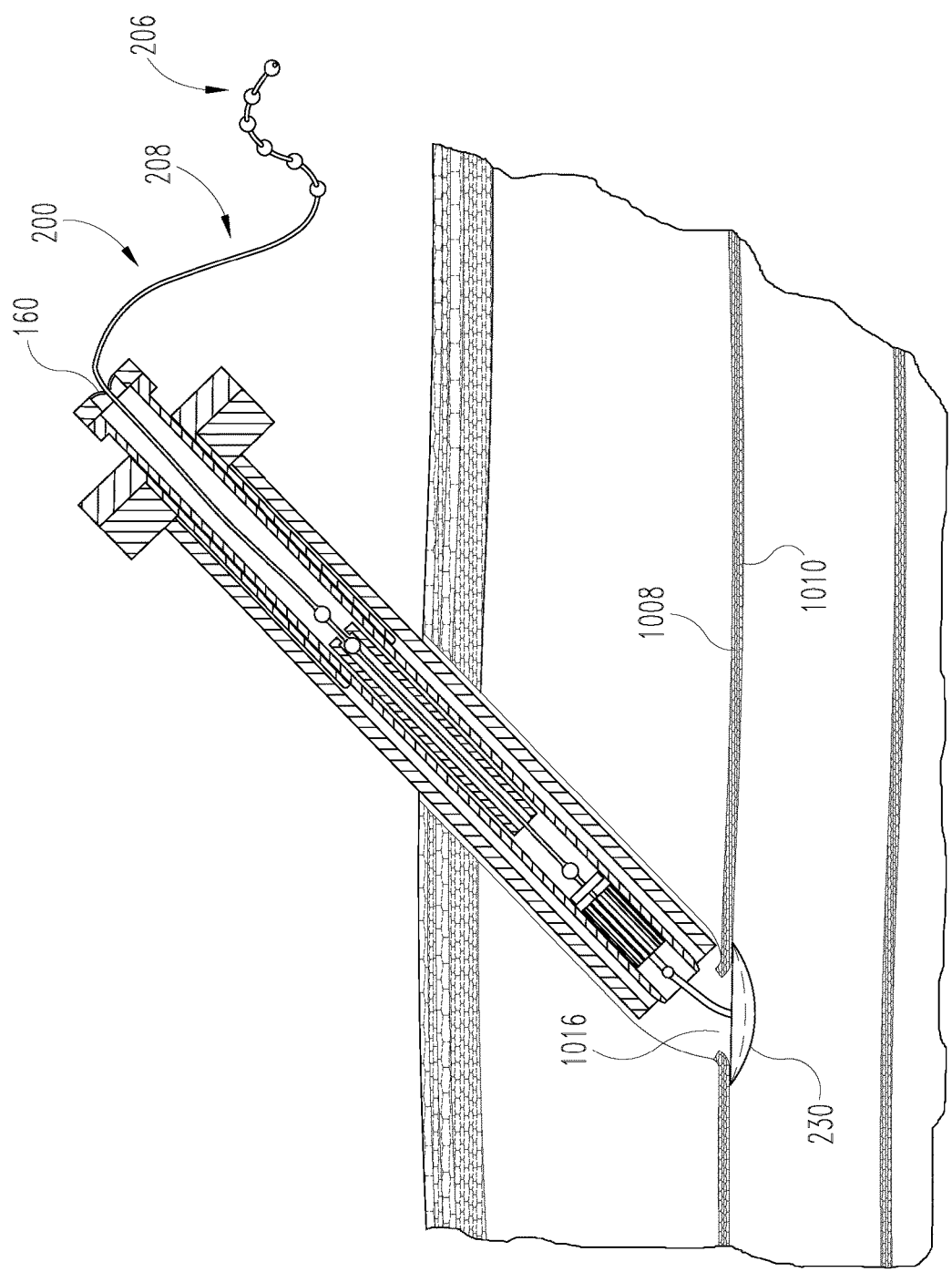
FIG. 27 is the system illustrated in FIG. 24, in a fourth position, with the vascular closure device retracted and contacting the inner surface of the vessel wall.

As shown in FIG. 27, as the resisting member 160, insertion sheath 140, introducer 110, and/or outer sheath 240 are being withdrawn, the resisting member 160 contacts the outer surface of the elongated body 200 in the low resistance portion 208 and imparts a resistive force onto the elongated body 200. The resistive force withdraws the elongated body 200 from the vessel 1006 so as to pull the vascular closure device 230 against the inner surface 1010 of the vessel wall 1008 thereby covering hole 1016

Figure 28:
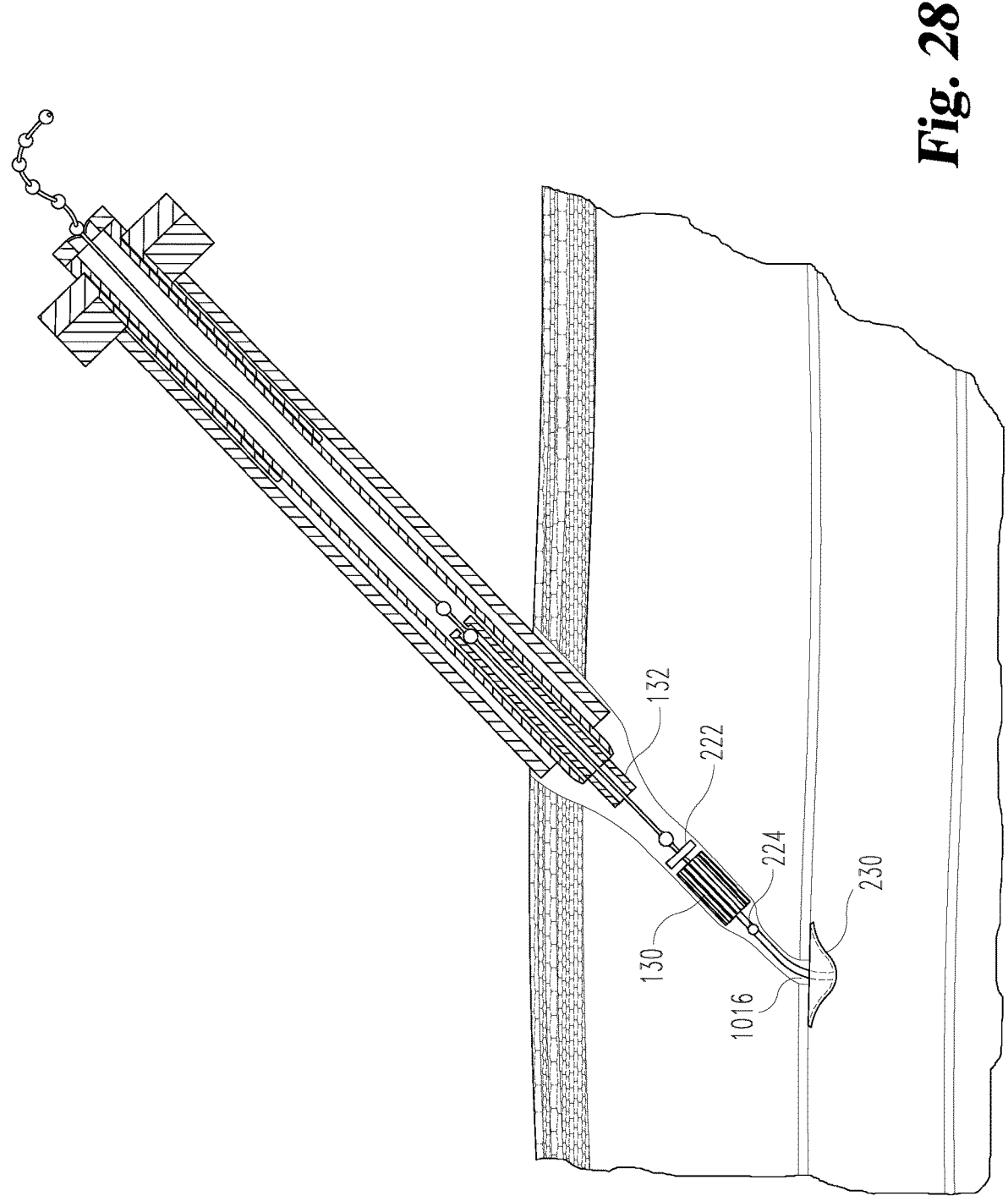
FIG. 28 is the system illustrated in FIG. 24 in a fifth position, with the vascular closure device in a conforming configuration upon application of a conforming force from the elongated body.

As vascular closure device 230 contacts the inner surface 1010 of the vessel wall 1008, the resisting member 160 slides along the elongated body 200. As the resisting member 160 slides from the low resistance portion 208 into the higher resistance portion 206 of the proximal end region 202, the force exerted to the vascular closure device 230 by the elongated body 200 increases to at least a conforming force but less than a deforming force, so as to conform the vascular closure device 230 to the inner surface 1010 of the vessel wall 1008, as shown in FIG. 28.

Figure 29:
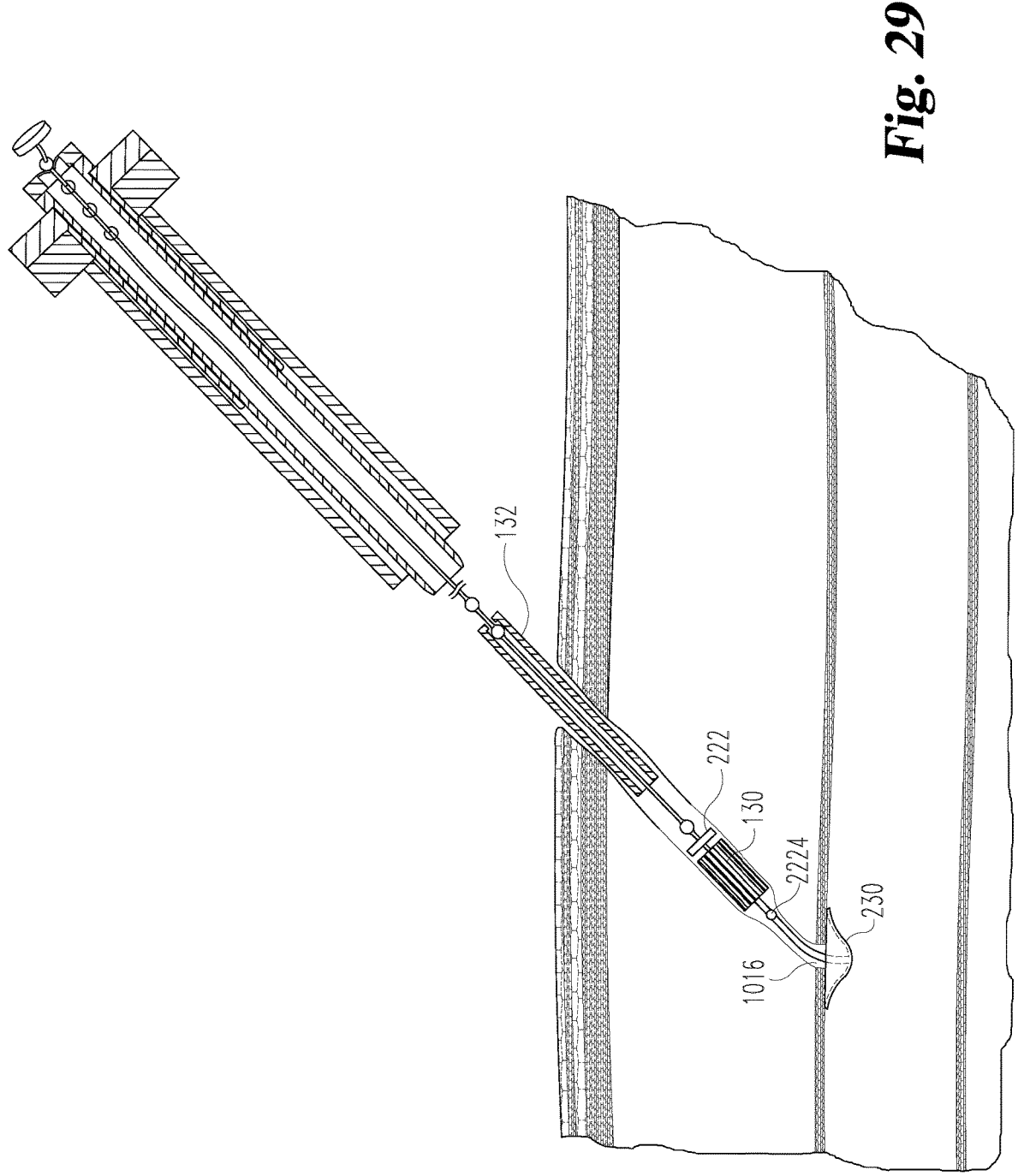
FIG. 29 is the system illustrated in FIG. 24 in a sixth position, with the outer sheath, the introducer, and the insertion sheath being withdrawn along the length of the elongated body, and a conforming force being applied to the vascular closure device.
Figure 30:
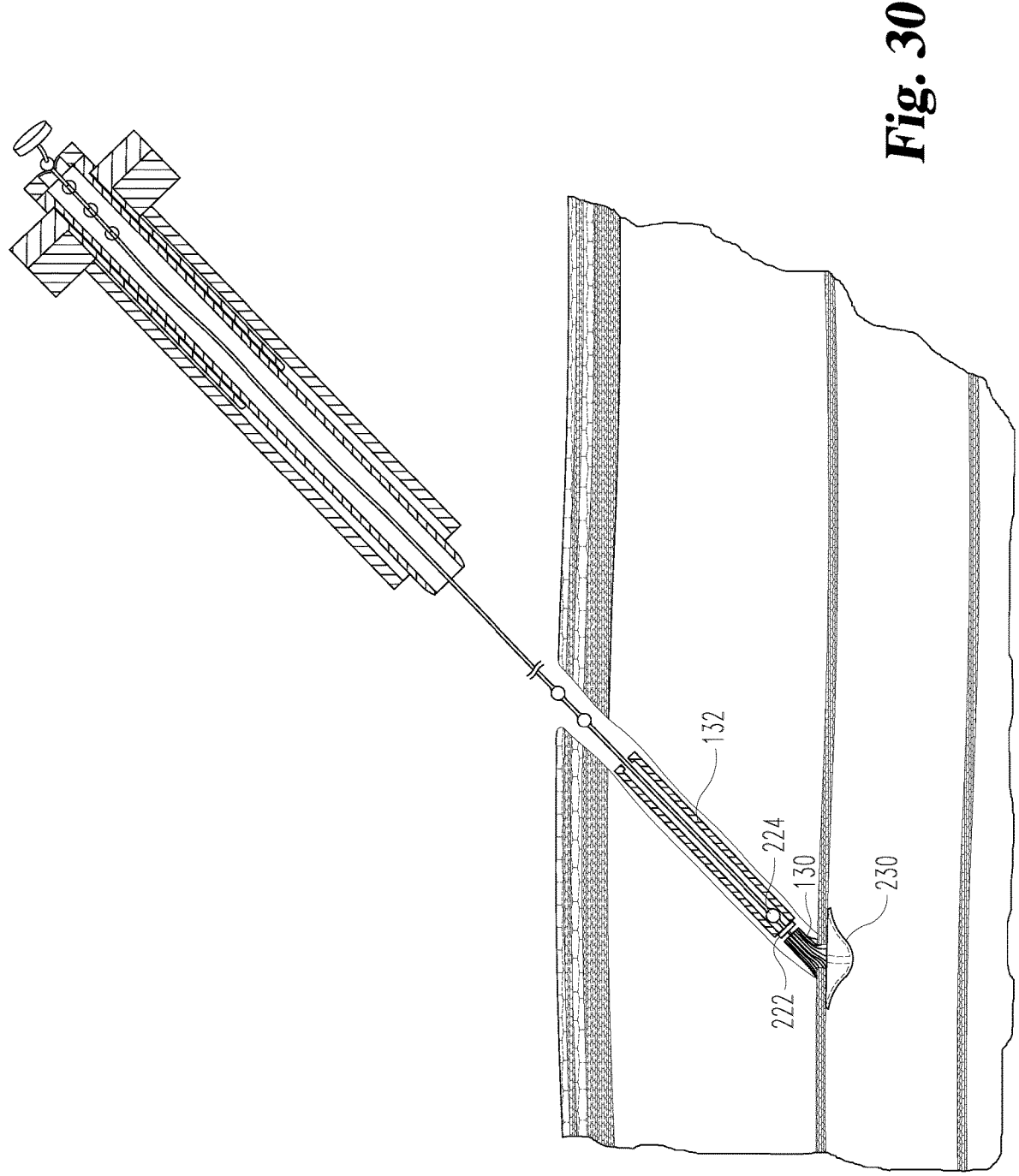
FIG. 30 is the system illustrated in FIG. 24 in a seventh position, with the packing member advanced over the elongated body and abutting against the outer surface of the vessel wall.

As illustrated in FIGS. 29 and 30, the operator continues to withdraw the insertion sheath 140, introducer 110 and/or the outer sheath 240 along the length of the elongated body 200 such that additional protrusions 210 of the high resistance portion 206 are moved through the resisting member 160. As the operator pulls on the outer sheath 240, introducer 110 and/or the insertion sheath 140 over the protrusions 210, an amount of force between the conforming force and deforming force is being applied through the elongated body 200 to the vascular closure device 230. At this time the operator advances a packing member 130 towards the hole 1016 in the vessel wall 1008 by pushing on a pushing member 132 along a length of the elongated body 200. When the operator is pleased with the positioning of the packing member 130, such as when the packing member 130 is coupled to the vessel 1006 by a locking member 222, the operator severs a portion of the elongated body 200 so as to leave the vascular closure device 230 in position against the inner surface 1010 of the vessel wall 1008 with the packing member 130 positioned against the outer surface 1012 of the vessel wall 1008 and a portion of the elongated body 200 in tensions between the vascular closure device 230 and the packing member 130. In this configuration, the portion of the elongated body 200 left in situ exerts a conforming force to the vascular closure device 230 and the packing member 130 so as to substantially occlude the hole in the vessel wall.

In some embodiments, the high resistance portion 206 of the elongated body 200, such as a protrusion 210, is constructed and arranged to compensate for the force exerted by the pushing member 132 to push the packing member 130 against the vessel wall 1008. In other words, the interaction between the resisting member 160 and the high resistance portion 206 is such that even when the operator is applying an opposing force to portions of the system 100 to secure the packing member 130 against the vessel wall 1008, the distal end 204 of the elongated body 200 still applies at least a conforming force to the vascular closure device 230.

While other devices rely on a clot forming at the opening in the wall of the vessel, and thus result in substantial oozing from the opening while a clot is forming, embodiments such as those noted above cover the inside of the opening. Closure is maintained by tension on the seal, and by deforming the seal so that a portion of it is held against the vessel by the reaction of the seal to the deformation.

While the subject matter herein has been illustrated and described in detail in the exemplary drawings and foregoing description, the same is to be considered as illustrative and not restrictive in character, it being understood that only the preferred embodiment(s) have been shown and described and that all changes and modifications that come within the spirit of the disclosure are desired to be protected. It will be understood that structures, methods or other features described particularly with one embodiment can be similarly used or incorporated in or with respect to other embodiments.

The invention claimed is:

1. An apparatus usable with an introducer that passes through a hole in a vessel wall of a vessel, the apparatus having a predeployment state and a deployed state, the apparatus comprising:
   a sleeve assembly defining a bore and comprising a proximal end and a distal end, wherein said sleeve assembly is adapted to be inserted into the introducer;

an elongated body comprising a proximal end region, a distal end region, a high-resistance portion in said proximal end region, and a low-resistance portion in said distal end region;

a vascular closure device coupled to a distal end of said elongated body, wherein said vascular closure device is adapted to occlude the hole when a conforming force is applied to said vascular closure device, wherein, in the predeployment state, said vascular closure device is contained inside the bore of said sleeve assembly and said high-resistance portion of said elongated body is positioned outside of said sleeve assembly and wherein, in the deployed state, said vascular closure device is outside of the bore of said sleeve assembly and inside the vessel; and a resisting member fixed to said sleeve assembly, wherein said elongated body slidably couples with and contacts said resisting member thereby generating a resistive force between said elongated body and said resisting member when said sleeve assembly and said resisting member are withdrawn away from the hole when said vascular closure device is inside the vessel, wherein the resistive force between said high-resistance portion and said resisting member is greater than the resistive force between said low-resistance portion and said resisting member.

2. The apparatus of claim 1, wherein the resistive force between said high-resistance portion and said resisting member is greater than the conforming force sufficient for said vascular closure device to conform to the inside of the vessel wall and occlude the hole in the vessel wall.

3. The apparatus of claim 2, wherein the resistive force between said high-resistance portion and said resisting member is less than a deforming force.

4. The apparatus of claim 1, wherein said high-resistance portion defines a large diameter portion and said low-resistance portion defines a small diameter portion smaller than said large diameter portion.

5. The apparatus of claim 1, further comprising:
a taper on said elongated body.

6. The apparatus of claim 1, further comprising:
a shoulder on said elongated body.

7. The apparatus of claim 1, wherein said high-resistance portion defines a plurality of large-diameter portions separated by small-diameter portions along a length of said elongated body.

8. The apparatus of claim 1, further comprising:
a stop member positioned at said proximal end region of said elongated body adapted to not pass through said resisting member.

9. The apparatus of claim 1, wherein said high-resistance portion comprises a surface that has an average surface roughness greater than that of said low-resistance portion.

10. The apparatus of claim 1, further comprising a locking member and a packing member, wherein said elongated body further comprises a protrusion and wherein said locking member is adapted to interface with said protrusion to resist movement of said packing member in a direction away from the vascular closure device.

11. The apparatus of claim 1, wherein said resisting member is positioned on the proximal end of said sleeve assembly.

12. The apparatus of claim 11, wherein said resisting member comprises a valve.

13. A system adapted to conform a vascular closure device over a hole in a vessel wall to occlude the hole, the system having a predeployment state and a deployed state, the system comprising:

a sleeve assembly defining a bore and comprising a proximal end and a distal end;

an elongated body comprising a proximal end region, a distal end region, a high-resistance portion in said proximal end region, and a low-resistance portion in said distal end region;

wherein a distal end of said elongated body is coupled to the vascular closure device, wherein, in the predeployment state, said vascular closure device is contained inside the bore of said sleeve assembly and said high-resistance portion of said elongated body is positioned outside of said sleeve assembly and wherein, in the deployed state, said vascular closure device is outside of the bore of said sleeve assembly and is positioned over the hole in the vessel wall; and a resisting member fixed to said sleeve assembly, wherein said elongated body slidably couples with and contacts said resisting member thereby generating a resistive force between said elongated body and said resisting member when said sleeve assembly and said resisting member are withdrawn away from the hole when said vascular closure is positioned over the hole in the vessel wall, wherein the resistive force between said high-resistance portion and said resisting member is greater than the resistive force between said low-resistance portion and said resisting member.

14. The system of claim 13, wherein said resisting member comprises a valve.

15. The system of claim 13, wherein said resisting member comprises a channel arranged to receive said elongated body, wherein said channel changes directions along at least one axis.

16. The system of claim 13, wherein said resisting member comprises a spring-loaded friction system comprising a first surface, a second surface, and a spring member biasing said first surface towards said second surface.

17. A system adapted to conform a vascular closure device over a hole in a vessel wall to occlude the hole, the system having a predeployment state and a deployed state, the system comprising:

a sleeve assembly defining a bore and comprising a proximal end and a distal end;

an elongated body comprising a proximal end region, a distal end and a distal end region, said distal end coupled to the vascular closure device, wherein, in the predeployment state, the vascular closure device is contained inside the bore of said sleeve assembly and wherein, in the deployed state, the vascular closure device is outside of the bore of said sleeve assembly; and a resisting member fixed to said sleeve assembly that slidably couples with and contacts said elongated body thereby generating a resistive force that resists relative longitudinal movement between the elongated body and the resisting member when said sleeve assembly and said resisting member are withdrawn away from said vascular closure device when said vascular closure device is positioned over the hole in the vessel wall, wherein the resistive force has a maximum static resistive force during a non-sliding condition and a maximum dynamic resistive force during a sliding condition and wherein the maximum static resistive force is greater than a conforming force sufficient to conform the vascular closure device over the hole and is less than a deforming force of the vascular closure device.

18. The system of claim 17, wherein the maximum dynamic resistive force is greater than the conforming force sufficient to conform the vascular closure device over the hole.

19. The system of claim 17, wherein the maximum dynamic resistive force is less than the deforming force of the vascular closure device.

20. The system of claim 17, wherein the maximum resistive force is variable.

21. The system of claim 17, wherein said sleeve assembly is adapted to be inserted into an introducer to deploy the vascular closure device through the hole in the vessel wall.

\* \* \* \* \*